US012788530B2

(12) United States Patent
Wolf et al.

(10) Patent No.: US 12,788,530 B2
(45) Date of Patent: Nov. 10, 2026

(54) ANALYSIS OF VIDEO DATA FOR ADDRESSING TIME SENSITIVE SITUATIONS IN SURGICAL PROCEDURES

(71) Applicant: Theator Inc., Palo Alto, CA (US)

(72) Inventors: Tamir Wolf, Palo Alto, CA (US); Dotan Asselmann, Holon (IL); Alenka Antolin, Ljubljana (SI); Evgeny Makrinich, Tel Aviv (IL); Kavi Vyas, San Francisco, CA (US); Daniel Neimark, Tel Aviv (IL)

(73) Assignee: Theator, Inc., Palo Alto, CA (US)

( * ) Notice: Subject to any disclaimer, the term of this patent is extended or adjusted under 35 U.S.C. 154(b) by 320 days.

(21) Appl. No.: 18/294,089

(22) PCT Filed: Aug. 16, 2022

(86) PCT No.: PCT/US2022/075011
§ 371 (c)(1),
(2) Date: Jan. 31, 2024

(87) PCT Pub. No.: WO2023/023509
PCT Pub. Date: Feb. 23, 2023

(65) Prior Publication Data
US 2024/0390103 A1 Nov. 28, 2024

Related U.S. Application Data

(60) Provisional application No. 63/302,155, filed on Jan. 24, 2022, provisional application No. 63/233,871, filed on Aug. 17, 2021.

(51) Int. Cl.
*A61B 90/00* (2016.01)
*G16H 30/40* (2018.01)
*A61B 34/20* (2016.01)

(52) U.S. Cl.
CPC .......... *A61B 90/361* (2016.02); *G16H 30/40* (2018.01); *A61B 2034/2055* (2016.02)

(58) Field of Classification Search
CPC .......... A61B 90/361; A61B 2034/2055; A61B 90/30; A61B 2017/00216;
(Continued)

(56) References Cited

U.S. PATENT DOCUMENTS 5,791,907 A 8/1998 Ramshaw et al.
8,886,577 B2 11/2014 Mangione-Smith
(Continued)

FOREIGN PATENT DOCUMENTS

CA 2575759 A1 2/2006
CA 3049148 A1 8/2018
(Continued)

OTHER PUBLICATIONS

Bhatia et al., "Real-Time Identification of Operating Room State from Video," Conference: Proceedings of the Twenty-Second AAAI Conference on Artificial Intelligence 1761-1766 (Jul. 2007) (Year: 2007).

(Continued)

*Primary Examiner* — Edward Park
*Assistant Examiner* — Alexander Joseph Vaughn
(74) *Attorney, Agent, or Firm* — FINNEGAN, HENDERSON, FARABOW, GARRETT & DUNNER, L.L.P.

(57) ABSTRACT

Systems, methods, and non-transitory computer readable media for automated analysis of video data during surgical procedures using artificial intelligence are provided. Surgical footage of an ongoing surgical procedure may be received and analyzed. The analysis may detect prospective adverse actions in surgical procedures based on the presence of a surgical instrument in a surgical cavity and a phase of
(Continued)

the ongoing surgical procedure. The analysis may trigger removal of tissue for biopsy in an ongoing surgical procedure based on a likelihood that a feasible biopsy will cause a diagnosis of a condition other than a known condition of the patient. The analysis may facilitate addressing time sensitive situations in surgical procedures, for example by providing notification when no action to address a time sensitive situation is initiated within the selected time period.

20 Claims, 8 Drawing Sheets

(58) Field of Classification Search
CPC ........ A61B 2090/365; A61B 2090/371; A61B 2034/2065; G16H 30/40; G16H 20/40; G16H 15/00; G16H 40/60; G16H 50/20
See application file for complete search history.

(56) References Cited

U.S. PATENT DOCUMENTS

| | | | |
|---|---|---|---|
| 9,788,907 | B1 | 10/2017 | Alvi et al. |
| 9,836,654 | B1 | 12/2017 | Alvi et al. |
| 10,387,720 | B2 | 8/2019 | Johnson et al. |
| 10,646,156 | B1 | 5/2020 | Schnorr |
| 10,729,502 | B1 | 8/2020 | Wolf et al. |
| 10,791,301 | B1 | 9/2020 | Kilroy et al. |
| 10,878,966 | B2 | 12/2020 | Wolf et al. |
| 10,886,015 | B2 | 1/2021 | Wolf et al. |
| 10,943,682 | B2 | 3/2021 | Wolf et al. |
| 11,065,079 | B2 | 7/2021 | Wolf et al. |
| 11,116,587 | B2 | 9/2021 | Wolf et al. |
| 2002/0172498 | A1 | 11/2002 | Esenyan et al. |
| 2004/0062381 | A1 | 4/2004 | Shambaugh et al. |
| 2004/0078236 | A1 | 4/2004 | Stoodley et al. |
| 2004/0125121 | A1 | 7/2004 | Pea et al. |
| 2005/0149361 | A1 | 7/2005 | Saus et al. |
| 2006/0143060 | A1 | 6/2006 | Conry et al. |
| 2006/0159325 | A1 | 7/2006 | Zeineh et al. |
| 2007/0156344 | A1 | 7/2007 | Sender et al. |
| 2008/0140444 | A1* | 6/2008 | Karkanias .............. G16H 10/20 705/2 |
| 2008/0243064 | A1 | 10/2008 | Stahler et al. |
| 2009/0192823 | A1 | 7/2009 | Hawkins et al. |
| 2009/0299924 | A1 | 12/2009 | Dean et al. |
| 2009/0300507 | A1 | 12/2009 | Raghavan et al. |
| 2010/0001149 | A1 | 1/2010 | Song et al. |
| 2010/0036676 | A1 | 2/2010 | Safdi et al. |
| 2010/0134609 | A1 | 6/2010 | Johnson |
| 2011/0046476 | A1 | 2/2011 | Cinquin et al. |
| 2011/0090367 | A1 | 4/2011 | White et al. |
| 2011/0225000 | A1 | 9/2011 | Selim |
| 2011/0264528 | A1 | 10/2011 | Whale et al. |
| 2011/0276340 | A1 | 11/2011 | DeBoer et al. |
| 2011/0276348 | A1 | 11/2011 | Ahn et al. |
| 2011/0306985 | A1 | 12/2011 | Inoue et al. |
| 2012/0035963 | A1 | 2/2012 | Qian et al. |
| 2012/0177256 | A1 | 7/2012 | Keefe et al. |
| 2012/0179061 | A1 | 7/2012 | Ramanan et al. |
| 2013/0132117 | A1 | 5/2013 | Barsoum et al. |
| 2013/0288214 | A1 | 10/2013 | Kesavadas et al. |
| 2013/0297343 | A1 | 11/2013 | Hirose et al. |
| 2014/0081659 | A1 | 3/2014 | Nawana et al. |
| 2014/0101550 | A1 | 4/2014 | Zises |
| 2014/0226888 | A1 | 8/2014 | Skidmore |
| 2014/0270711 | A1 | 9/2014 | Maser et al. |
| 2014/0276940 | A1 | 9/2014 | Seo |
| 2014/0286533 | A1 | 9/2014 | Luo et al. |
| 2014/0297301 | A1 | 10/2014 | Rock |
| 2015/0046182 | A1 | 2/2015 | Kinney et al. |
| 2015/0119705 | A1 | 4/2015 | Tochterman et al. |
| 2015/0190208 | A1 | 7/2015 | Silviera |
| 2016/0004911 | A1 | 1/2016 | Cheng et al. |
| 2016/0067007 | A1 | 3/2016 | Piron et al. |
| 2016/0191887 | A1 | 6/2016 | Casas |
| 2016/0239617 | A1 | 8/2016 | Farooq et al. |
| 2016/0253472 | A1 | 9/2016 | Pederson et al. |
| 2016/0259888 | A1 | 9/2016 | Liu et al. |
| 2017/0053543 | A1 | 2/2017 | Argawal et al. |
| 2017/0071679 | A1 | 3/2017 | Weir et al. |
| 2017/0083665 | A1 | 3/2017 | Florin et al. |
| 2017/0119258 | A1 | 5/2017 | Kotanko et al. |
| 2017/0132785 | A1 | 5/2017 | Wshah et al. |
| 2017/0177806 | A1 | 6/2017 | Fabian |
| 2017/0249432 | A1 | 8/2017 | Grantcharov |
| 2017/0300651 | A1 | 10/2017 | Strobridge |
| 2017/0312031 | A1 | 11/2017 | Amanatullah et al. |
| 2018/0065248 | A1 | 3/2018 | Barral et al. |
| 2018/0078195 | A1 | 3/2018 | Sutaria et al. |
| 2018/0110398 | A1 | 4/2018 | Schwartz et al. |
| 2018/0122506 | A1 | 5/2018 | Grantcharov et al. |
| 2018/0158361 | A1 | 6/2018 | Goll et al. |
| 2018/0174311 | A1 | 6/2018 | Kluckner et al. |
| 2018/0174616 | A1 | 6/2018 | Aguilar et al. |
| 2018/0197624 | A1 | 7/2018 | Robaina et al. |
| 2018/0247024 | A1 | 8/2018 | Divine et al. |
| 2018/0247128 | A1 | 8/2018 | Alvi et al. |
| 2018/0247560 | A1 | 8/2018 | Mackenzie et al. |
| 2018/0303552 | A1 | 10/2018 | Ryan et al. |
| 2018/0322949 | A1 | 11/2018 | Mohr et al. |
| 2018/0350144 | A1 | 12/2018 | Rathod |
| 2018/0366231 | A1 | 12/2018 | Wolf et al. |
| 2018/0368930 | A1 | 12/2018 | Esterberg et al. |
| 2019/0005848 | A1 | 1/2019 | Kilroy et al. |
| 2019/0006047 | A1 | 1/2019 | Gorek et al. |
| 2019/0019574 | A1 | 1/2019 | Byrnes |
| 2019/0060893 | A1 | 2/2019 | Evans et al. |
| 2019/0090969 | A1 | 3/2019 | Jarc et al. |
| 2019/0122330 | A1 | 4/2019 | Saget et al. |
| 2019/0125361 | A1 | 5/2019 | Shelton, IV et al. |
| 2019/0201136 | A1 | 7/2019 | Shelton, IV et al. |
| 2019/0201141 | A1 | 7/2019 | Shelton, IV et al. |
| 2019/0201144 | A1 | 7/2019 | Shelton, IV et al. |
| 2019/0206565 | A1 | 7/2019 | Shelton, IV |
| 2019/0223961 | A1 | 7/2019 | Barral et al. |
| 2019/0272917 | A1 | 9/2019 | Couture et al. |
| 2019/0279765 | A1 | 9/2019 | Giataganas et al. |
| 2019/0286652 | A1 | 9/2019 | Habbecke |
| 2019/0347557 | A1 | 11/2019 | Khan et al. |
| 2019/0362834 | A1 | 11/2019 | Venkataraman et al. |
| 2019/0362859 | A1 | 11/2019 | Bhat |
| 2019/0365252 | A1 | 12/2019 | Fernald et al. |
| 2019/0371456 | A1 | 12/2019 | Page et al. |
| 2019/0380792 | A1 | 12/2019 | Poltaretskyi et al. |
| 2020/0027211 | A1 | 1/2020 | Dufort |
| 2020/0030044 | A1 | 1/2020 | Wang et al. |
| 2020/0168334 | A1 | 5/2020 | Mowery |
| 2020/0194111 | A1 | 6/2020 | Venkataraman et al. |
| 2020/0211720 | A1 | 7/2020 | Goldberg |
| 2020/0226751 | A1 | 7/2020 | Jin et al. |
| 2020/0237452 | A1 | 7/2020 | Wolf et al. |
| 2020/0258616 | A1 | 8/2020 | Likosky et al. |
| 2020/0268457 | A1 | 8/2020 | Wolf et al. |
| 2020/0268469 | A1 | 8/2020 | Wolf et al. |
| 2020/0268472 | A1 | 8/2020 | Wolf et al. |
| 2020/0272660 | A1 | 8/2020 | Wolf et al. |
| 2020/0273548 | A1 | 8/2020 | Wolf et al. |
| 2020/0273552 | A1 | 8/2020 | Wolf et al. |
| 2020/0273557 | A1 | 8/2020 | Wolf et al. |
| 2020/0273560 | A1 | 8/2020 | Wolf et al. |
| 2020/0273561 | A1 | 8/2020 | Wolf et al. |
| 2020/0273563 | A1 | 8/2020 | Wolf et al. |
| 2020/0273575 | A1 | 8/2020 | Wolf et al. |
| 2020/0273577 | A1 | 8/2020 | Wolf et al. |
| 2020/0273581 | A1 | 8/2020 | Wolf et al. |
| 2020/0335208 | A1* | 10/2020 | Talmor .................. G06V 20/52 |
| 2020/0337648 | A1 | 10/2020 | Saripalli et al. |
| 2021/0012868 | A1 | 1/2021 | Wolf et al. |
| 2021/0015560 | A1 | 1/2021 | Boddington et al. |
| 2021/0158845 | A1 | 5/2021 | Sethi et al. |
| 2021/0290046 | A1 | 9/2021 | Nazareth et al. |
| 2021/0298869 | A1 | 9/2021 | Wolf et al. |

(56) References Cited

U.S. PATENT DOCUMENTS

| | | | |
|---|---|---|---|
| 2021/0307840 | A1 | 10/2021 | Wolf et al. |
| 2021/0307864 | A1 | 10/2021 | Wolf et al. |
| 2021/0312949 | A1 | 10/2021 | Chulev et al. |
| 2021/0313050 | A1 | 10/2021 | Wolf et al. |
| 2021/0313051 | A1 | 10/2021 | Asselmann et al. |
| 2021/0313052 | A1 | 10/2021 | Makrinich et al. |
| 2022/0165403 | A1 | 5/2022 | Wolf et al. |
| 2022/0301674 | A1 | 9/2022 | Wolf et al. |
| 2023/0401649 | A1 | 12/2023 | Wolf et al. |

FOREIGN PATENT DOCUMENTS

| | | | |
|---|---|---|---|
| CN | 101588766 | A | 11/2009 |
| CN | 104411226 | A | 3/2015 |
| CN | 108472084 | A | 8/2018 |
| CN | 108475532 | A | 8/2018 |
| JP | 2003-263495 | A | 9/2003 |
| JP | 2015-097065 | A | 5/2015 |
| WO | WO 2017/066565 | A1 | 5/2015 |
| WO | WO 2017/031175 | A1 | 2/2017 |
| WO | WO 2018/089816 | A2 | 5/2018 |
| WO | WO 2019/040705 | A1 | 2/2019 |
| WO | WO 2019/079430 | A1 | 4/2019 |
| WO | WO 2019/139478 | A1 | 7/2019 |
| WO | WO 2019/226182 | A1 | 11/2019 |
| WO | WO 2020/023740 | A1 | 1/2020 |
| WO | WO 2020/172414 | A1 | 8/2020 |
| WO | WO 2021/207016 | A1 | 10/2021 |
| WO | WO 2023/023509 | A1 | 2/2023 |

OTHER PUBLICATIONS

Communication and Search Report, dated Jun. 17, 2022, issued from the European Patent Office in International Application No. 20711478.6-1126 (21 pages).

Hall, Dr. Jena Mae, "Enhancing surgical education using video playback: A case study on the influence of video playback on the nature and experience of feedback between supervising surgeons and surgical residents", Queen's University, Kingston, Ontario, Canada, Sep. 2018, pp. 1-163. (Year: 2018).

Hassan et al., High Efficiency Video Coding (HEVC)-Based Surgical Telementoring System Using Shallow Convolution al Neural Network. J Digit Imaging 31, 1027-1043 (2019). https://dol.org/10.1007/s10278-019-00206.2 (Year: 2019).

International Search Report and Written Opinion of the International Search Authority in PCT/182021 /025522, mailed Sep. 6, 2021 (19 pages).

International Search Report and Written Opinion, issued from the European Patent Office in International Application No. PCT/US2020/019050, mailed Jun. 7, 2020 (24 pages).

International Search Report and Written Opinion of the International Search Authority in International Application No. PCT/US2022/075011 mailed Jan. 23, 2023 (16 pages).

Jin et al., "Tool Detection and Operative Skill Assessment in Surgical Videos Using Region-Based Convolutional Neural Networks," 2018 IEEE Winter Conference on Applications of Computer Vision (WACV), 2018. pp. 691-699, dol: 10.1109IVACV.

Loukas, C. Video content analysis of surgical procedures. Surg Endosc 32, 553-568 (2018). https://doi.org/10.1007 /s00464-017-5878-1 (Year: 2018).

Mackenzie et al., "Video Analysis: An Approach for Use in Health Care"; Handbook of Human Factors and Ergonomics in Health Care and Patient Safety, Second Edition; CRC Press, Aug. 3, 2011; pp. 523-541.

Münzer et al., "Domain-Specific Video Compression for Long-term Archiving of Endoscopic Surgery Videos", 2016 IEEE international Symposium on Computer-Based Medical Systems, Jun. 20, 2016, pp. 312-317.

Munzer et al., "EndoXplore: A Web-Based Video Explorer for Endoscopic Videos", 2017 IEEE International Symposium on Multimedia (ISM), Dec. 11, 2017, pp. 366-367.

Niitsu H, Hirabayashi N, Yoshimitsu M, et al., "Using the Objective Structured Assessment of Technical Skills (OSATS) Global Rating Scale to Evaluate the Skills of Surgical Trainees in the Operating Room", Surg Today 2013;43(3):271-275, doi: 10.1007/s00595-012-OS 13-7 (Year: 2013).

Padoy, Nicholas, "Workflow and Activity Modeling for Monitoring Surgical Procedures," Apr. 14, 2010, 1-137, Université de Lorraine, Nancy, France.

Petscharnig et al., "Learning Laparoscopic Video Shot Classification for Gynecological Surgery," Multimed. Tools Appl., vol. 77, pp. 8061-8097 (2018).

Twinanda et al., "RSDNet: Learning to Predict Remaining Surgery Duration from Laparoscopic Videos Without Manual Annotations," 38(4) IEEE Trans Med Imaging 1069-1078 (Oct. 25, 2018) (Year: 2018).

* cited by examiner

501

511

512D

| Record Number | Procedure | Age | Gender | Medical Considerations | Time | Other Data |
|---|---|---|---|---|---|---|
| 1 | Bypass Surgery | 65 | M | Renal Disease | 4 hours | 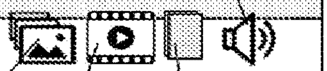 |
| 2 | Bypass Surgery | 78 | F | None | 3 hours | |

512A 512B 512C

513

| Record Number | Procedure | Surgeon Name |
|---|---|---|
| 1 | Bypass Surgery | Dr. Mac |
| 2 | Bypass Surgery | Dr. Doe |

Fig. 5

600

| Video Footage | Footage Location | Phase Tag | Event Location | Event Tag | Event Characteristic |
|---|---|---|---|---|---|
| 610 LaparoscopicCholecysectomy_11_24_2019.mp4 | 0:38:02 – 1:04:36 | Calot's triangle dissection | 0:43:09 | Incision | Skill level: 8 |
| LaparoscopicCholecysectomy_11_24_2019.mp4 | 1:04:36 – 1:23:16 | Cutting of cystic duct | 1:08:39 | Incision | Skill level: 7 |
| 620 CataractSurgery_03_11_2019.mp4 | 0:12:32 – 0:39:59 | Corneal incision | 0:22:56 | Incision | Skill level: 9 |
| ... | | | | | |

621 622 623 624 625

Fig. 6

ANALYSIS OF VIDEO DATA FOR ADDRESSING TIME SENSITIVE SITUATIONS IN SURGICAL PROCEDURES

CROSS-REFERENCES TO RELATED APPLICATIONS

This application is a national phase of PCT International Application No. PCT/US2022/075011, filed Aug. 16, 2022, which is based on and claims benefit of priority of U.S. Provisional Patent Application No. 63/233,871, filed Aug. 17, 2021; and U.S. Provisional Patent Application No. 63/302,155 filed Jan. 24, 2022. The contents of the foregoing applications are incorporated herein by reference in their entireties.

BACKGROUND

Technical Field

The disclosed embodiments generally relate to systems and methods for analysis of videos of surgical procedures.

Background Information

Correct performance of surgical procedures, including the performance of the different steps of a surgical procedure in the right time and order, depends on the surgeon performing the surgical procedure. While surgeons are highly skilled and trained to avoid errors, errors do occur, as in any other human activity. While the training reduces the number of errors, the errors that do occur in a surgical procedure may have dire consequences. Having a peer or a supervisor in the operating room while the surgical procedure is ongoing to warn before an action is about to take place at an unsuitable phase of the ongoing surgical procedure may reduce the number of errors. This is a common solution when training new surgeons. However, the time and effort required from the peers and supervisors to oversee all surgeries, even of senior surgeons, will be enormous. Therefore, it is beneficial to have an automated detection of prospective adverse actions in surgical procedures.

Typically, a surgery is a focused endeavor to achieve a desired predetermined goals. However, during surgery, opportunities to perform other unplanned actions that may benefit the patient may arise. For example, an opportunity to treat a previously unknown condition that was discovered during the surgery may arise. In another example, an opportunity to diagnose a previously unsuspected condition may arise, for example through biopsy. Unfortunately, in many cases the surgeon conducting the surgery are focused on the desired predetermined goals, and may miss the opportunities to perform other unplanned actions that may benefit the patient. It is therefore beneficial to automatically identify the opportunities to perform other unplanned actions that may benefit the patient, and to notify the surgeons about the identified opportunities.

In a surgical procedure, a surgeon may be faced with many situations that require attention simultaneously. Some of these situations may be time sensitive, where a delayed reaction may be harmful. However, notifying the surgeon about all situations that require attention, or about all time sensitive situations, may result in clutter. It is therefore desired to identify the time sensitive situations that the surgeon is likely to miss, and notify the surgeon about these situations, possibly ignoring other situations or notifying about the other situations in a different, less intensive, way.

Therefore, there is a need for unconventional approaches that efficiently and effectively analyze surgical videos to enable a medical professional to receive support during an ongoing surgical procedure.

SUMMARY

Systems, methods, and non-transitory computer readable media for detecting prospective adverse actions in surgical procedures are disclosed. In some examples, surgical footage of an ongoing surgical procedure captured using at least one image sensor in an operating room may be received. The surgical footage may be analyzed to detect a presence of a surgical instrument in a surgical cavity at a particular time. The surgical footage may be analyzed to determine a phase of the ongoing surgical procedure at the particular time. Further, based on the presence of the surgical instrument in the surgical cavity at the particular time and the determined phase of the ongoing surgical procedure at the particular time, a likelihood that a prospective action involving the surgical instrument is about to take place at an unsuitable phase of the ongoing surgical procedure may be determined.

Systems, methods, and non-transitory computer readable media for triggering removal of tissue for biopsy in an ongoing surgical procedure are disclosed. In some examples, surgical footage of an ongoing surgical procedure performed on a patient may be received. The surgical footage may be surgical footage captured using at least one image sensor in an operating room. The ongoing surgical procedure may be associated with a known condition of the patient. The surgical footage may be analyzed to determine a likelihood that a feasible biopsy will cause a diagnosis of a condition other than the known condition of the patient. Further, based on the determined likelihood, a digital signal configured to cause a removal of a sample of a tissue for the feasible biopsy during the ongoing surgical procedure may be provided.

Systems, methods, and non-transitory computer readable media for addressing time sensitive situations in surgical procedures are disclosed. First surgical footage captured using at least one image sensor from an ongoing surgical procedure may be received. The first surgical footage may be analyzed to identify a time sensitive situation. A time period for initiating an action to address the time sensitive situation may be selected. Second surgical footage captured using the at least one image sensor from the ongoing surgical procedure after the identification of the time sensitive situation may be received. The second surgical footage may be analyzed to determine that no action to address the time sensitive situation was initiated within the selected time period. Further, in response to the determination that no action to address the time sensitive situation was initiated within the selected time period, information indicative of a need to address the time sensitive situation may be provided.

BRIEF DESCRIPTION OF THE DRAWINGS

FIG. 5 is a table view of an exemplary data structure consistent with disclosed embodiments.

FIG. 6 is a table view of an exemplary data structure consistent with the disclosed embodiments.

DETAILED DESCRIPTION

Figure 1:
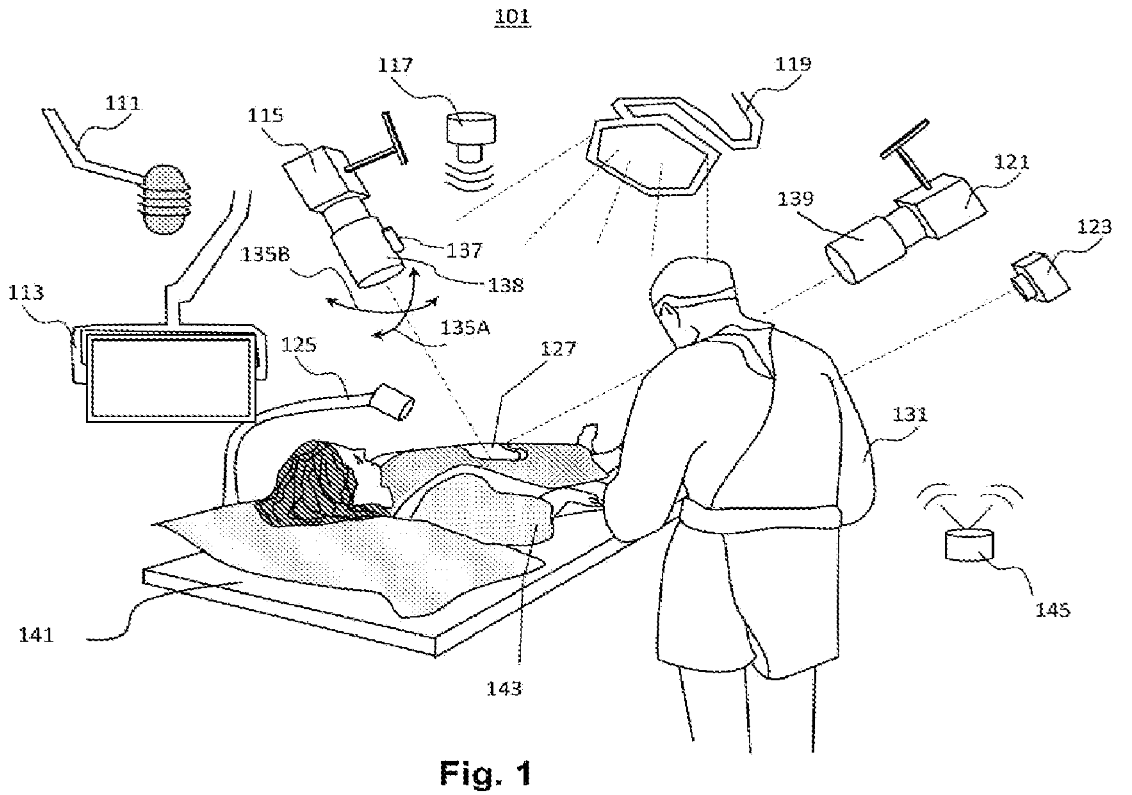
FIG. 1 is a perspective view of an example operating room, consistent with disclosed embodiments.

Unless specifically stated otherwise, as apparent from the following description, throughout the specification discussions utilizing terms such as "processing". "calculating", "computing", "determining", "generating", "setting", "configuring", "selecting", "defining", "applying", "obtaining", "monitoring", "providing". "identifying". "segmenting", "classifying", "analyzing", "associating", "extracting", "storing", "receiving", "transmitting", or the like, include actions and/or processes of a computer that manipulate and/or transform data into other data, the data represented as physical quantities, for example such as electronic quantities, and/or the data representing physical objects. The terms "computer", "processor", "controller", "processing unit", "computing unit", and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to features of "embodiments" "one case", "some cases", "other cases" or variants thereof means that a particular feature, structure or characteristic described may be included in at least one embodiment of the presently disclosed subject matter. Thus, the appearance of such terms does not necessarily refer to the same embodiment(s). As used herein, the term "and/or" includes any and all combinations of one or more of the associated listed items.

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

In some embodiments, a method, such as methods 700, 800 and 900, may comprise of one or more steps. In some examples, these methods, as well as all individual steps therein, may be performed by various aspects of computer system 410. For example, a system may comprise at least one processor, and the at least one processor may perform any of these methods as well as all individual steps therein, for example executing software instructions stored within memory devices. In some examples, these methods, as well as all individual steps therein, may be performed by a dedicated hardware. In some examples, a computer readable medium, such as a non-transitory computer readable medium, may store data and/or computer implementable instructions that, when executed by at least one processor, causes the at least one processor to carrying out any of these methods as well as all individual steps therein. Some non-limiting examples of possible execution manners of a method may include continuous execution (for example, returning to the beginning of the method once the method normal execution ends), periodically execution, executing the method at selected times, execution upon the detection of a trigger (some non-limiting examples of such trigger may include a trigger from a user, a trigger from another process, a trigger from an external device, etc.), and so forth.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term “data structure” as used herein in the singular is inclusive of plural data structures.

Analyzing the received video frames to identify surgical events may involve any form of electronic analysis using a computing device. In some embodiments, computer image analysis may include using one or more image recognition algorithms to identify features of one or more frames of the video footage. Computer image analysis may be performed on individual frames, or may be performed across multiple frames, for example, to detect motion or other changes between frames. In some embodiments, computer image analysis may include object detection algorithms, such as Viola-Jones object detection, scale-invariant feature transform (SIFT), histogram of oriented gradients (HOG) features, convolutional neural networks (CNN), or any other forms of object detection algorithms. Other example algorithms may include video tracking algorithms, motion detection algorithms, feature detection algorithms, color-based detection algorithms, texture-based detection algorithms, shape based detection algorithms, boosting based detection algorithms, face detection algorithms, biometric recognition algorithms, or any other suitable algorithm for analyzing video frames.

In some embodiments, the computer image analysis may include using a neural network model trained using example video frames including previously identified surgical events to thereby identify a similar surgical event in a set of frames. In other words, frames of one or more videos that are known to be associated with a particular surgical event may be used to train a neural network model. The trained neural network model may therefore be used to identify whether one or more video frames are also associated with the surgical event. In some embodiments, the disclosed methods may further include updating the trained neural network model based on at least one of the analyzed frames. Accordingly, by identifying surgical events in the plurality of surgical videos using computer image analysis, disclosed embodiments create efficiencies in data processing and video classification, reduces costs through automation, and improves accuracy in data classification.

Machine learning algorithms (also referred to artificial intelligence) may be employed for the purposes of analyzing the video to identify surgical events. Such algorithms be trained using training examples, such as described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters may be set manually by a person or automatically by a process external to the machine learning algorithm (such as a hyper parameter search algorithm), and the parameters of the machine learning algorithm may be set by the machine learning algorithm according to the training examples. In some implementations, the hyper-parameters may be set according to the training examples and the validation examples, and the parameters may be set according to the training examples and the selected hyper-parameters.

In some embodiments, trained machine learning algorithms (e.g., artificial intelligence algorithms) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image. In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

In some embodiments, analyzing image data (as described herein) may include analyzing the image data to obtain a preprocessed image data, and subsequently analyzing the image data and/or the preprocessed image data to obtain the desired outcome. Some non-limiting examples of such image data may include one or more images, videos, frames, footages, 2D image data, 3D image data, and so forth. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may include the transformed image data. For example, the transformed image data may include one or more convolutions of the image data. For example, the transformation function may comprise one or more image filters, such as low-pass filters, high-pass filters, band-pass filters, all-pass filters, and so forth. In some examples, the transformation function may include a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may include: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may include information based on and/or related to the extracted edges. In some examples, the image data may be preprocessed to extract image features from the image data. Some non-limiting examples of such image features may comprise information based on and/or related to: edges; corners; blobs; ridges; Scale Invariant Feature Transform (SIFT) features; temporal features; and so forth.

In some embodiments, analyzing image data (for example, by the methods, steps and processor function described herein) may include analyzing the image data and/or the preprocessed image data using one or more rules, functions, procedures, artificial neural networks, object detection algorithms, anatomical detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth.

In some embodiments, analyzing image data (for example, by the methods, steps and processor function described herein) may include analyzing pixels, voxels, point cloud, range data, etc. included in the image data.

A convolution may include a convolution of any dimension. A one-dimensional convolution is a function that transforms an original sequence of numbers to a transformed sequence of numbers. The one-dimensional convolution may be defined by a sequence of scalars. Each particular value in the transformed sequence of numbers may be determined by calculating a linear combination of values in a subsequence of the original sequence of numbers corresponding to the particular value. A result value of a calculated convolution may include any value in the transformed sequence of numbers. Likewise, an n-dimensional convolution is a function that transforms an original n-dimensional array to a transformed array. The n-dimensional convolution may be defined by an n-dimensional array of scalars (known as the kernel of the n-dimensional convolution). Each particular value in the transformed array may be determined by calculating a linear combination of values in an n-dimensional region of the original array corresponding to the particular value. A result value of a calculated convolution may include any value in the transformed array. In some examples, an image may comprise one or more components (such as color components, depth component, etc.), and each component may include a two dimensional array of pixel values. In one example, calculating a convolution of an image may include calculating a two dimensional convolution on one or more components of the image. In another example, calculating a convolution of an image may include stacking arrays from different components to create a three dimensional array, and calculating a three dimensional convolution on the resulting three dimensional array. In some examples, a video may comprise one or more components (such as color components, depth component, etc.), and each component may include a three dimensional array of pixel values (with two spatial axes and one temporal axis). In one example, calculating a convolution of a video may include calculating a three dimensional convolution on one or more components of the video. In another example, calculating a convolution of a video may include stacking arrays from different components to create a four dimensional array, and calculating a four dimensional convolution on the resulting four dimensional array.

Aspects of this disclosure may relate to surgical procedures performed in operating rooms. FIG. 1 shows an example operating room 101, consistent with disclosed embodiments. A patient 143 is illustrated on an operating table 141. Room 101 may include audio sensors, video/image sensors, chemical sensors, and other sensors, as well as various light sources (e.g., light source 119 is shown in FIG. 1) for facilitating the capture of video and audio data, as well as data from other sensors, during the surgical procedure. For example, room 101 may include one or more microphones (e.g., audio sensor 111, as shown in FIG. 1), several cameras (e.g., overhead cameras 115, 121, and 123, and a tableside camera 125) for capturing video/image data during surgery. While some of the cameras (e.g., cameras 115, 123 and 125) may capture video/image data of operating table 141 (e.g., the cameras may capture the video/image data at a location 127 of a body of patient 143 on which a surgical procedure is performed), camera 121 may capture video/image data of other parts of operating room 101. For instance, camera 121 may capture video/image data of a surgeon 131 performing the surgery. In some cases, cameras may capture video/image data associated with surgical team personnel, such as an anesthesiologist, nurses, surgical tech and the like located in operating room 101. Additionally, operating room cameras may capture video/image data associated with medical equipment located in the room.

In various embodiments, one or more of cameras 115, 121, 123 and 125 may be movable. For example, as shown in FIG. 1, camera 115 may be rotated as indicated by arrows 135A showing a pitch direction, and arrows 135B showing a yaw direction for camera 115. In various embodiments, pitch and yaw angles of cameras (e.g., camera 115) may be electronically controlled such that camera 115 points at a region-of-interest (ROI), of which video/image data needs to be captured. For example, camera 115 may be configured to track a surgical instrument (also referred to as a surgical tool) within location 127, an anatomical structure, a hand of surgeon 131, an incision, a movement of anatomical structure, and the like. In various embodiments, camera 115 may be equipped with a laser 137 (e.g., an infrared laser) for precision tracking. In some cases, camera 115 may be tracked automatically via a computer-based camera control application that uses an image recognition algorithm for positioning the camera to capture video/image data of a ROI. For example, the camera control application may identify an anatomical structure, identify a surgical tool, hand of a surgeon, bleeding, motion, and the like at a particular location within the anatomical structure, and track that location with camera 115 by rotating camera 115 by appropriate yaw and pitch angles. In some embodiments, the camera control application may control positions (i.e., yaw and pitch angles) of various cameras 115, 121, 123 and 125 to capture video/image date from different ROIs during a surgical procedure. Additionally or alternatively, a human operator may control the position of various cameras 115, 121, 123 and 125, and/or the human operator may supervise the camera control application in controlling the position of the cameras.

Cameras 115, 121, 123 and 125 may further include zoom lenses for focusing in on and magnifying one or more ROIs. In an example embodiment, camera 115 may include a zoom lens 138 for zooming closely to a ROI (e.g., a surgical tool in the proximity of an anatomical structure). Camera 121 may include a zoom lens 139 for capturing video/image data from a larger area around the ROI. For example, camera 121 may capture video/image data for the entire location 127. In some embodiments, video/image data obtained from camera 121 may be analyzed to identify a ROI during the surgical procedure, and the camera control application may be configured to cause camera 115 to zoom towards the ROI identified by camera 121.

In various embodiments, the camera control application may be configured to coordinate the position, focus, and magnification of various cameras during a surgical procedure. For example, the camera control application may direct camera 115 to track an anatomical structure and may direct camera 121 and 125 to track a surgical instrument. Cameras 121 and 125 may track the same ROI (e.g., a surgical instrument) from different view angles. For example, video/image data obtained from different view angles may be used to determine the position of the surgical instrument relative to a surface of the anatomical structure, to determine a condition of an anatomical structure, to determine pressure applied to an anatomical structure, or to determine any other information where multiple viewing angles may be beneficial. By way of another example, bleeding may be detected by one camera, and one or more other cameras may be used to identify the source of the bleeding.

In various embodiments, control of position, orientation, settings, and/or zoom of cameras 115, 121, 123 and 125 may be rule-based and follow an algorithm developed for a given surgical procedure. For example, the camera control application may be configured to direct camera 115 to track a surgical instrument, to direct camera 121 to location 127, to direct camera 123 to track the motion of the surgeon's hands, and to direct camera 125 to an anatomical structure. The algorithm may include any suitable logical statements determining position, orientation, settings and/or zoom for cameras 115, 121, 123 and 125 depending on various events during the surgical procedure. For example, the algorithm may direct at least one camera to a region of an anatomical structure that develops bleeding during the procedure. Some non-limiting examples of settings of cameras 115, 121, 123 and 125 that may be controlled (for example by the camera control application) may include image pixel resolution, frame rate, image and/or color correction and/or enhancement algorithms, zoom, position, orientation, aspect ratio, shutter speed, aperture, focus, and so forth.

In various cases, when a camera (e.g., camera 115) tracks a moving or deforming object (e.g., when camera 115 tracks a moving surgical instrument, or a moving/pulsating anatomical structure), a camera control application may determine a maximum allowable zoom for camera 115, such that the moving or deforming object does not escape a field of view of the camera. In an example embodiment, the camera control application may initially select the first zoom for camera 115, evaluate whether the moving or deforming object escapes the field of view of the camera, and adjust the zoom of the camera as necessary to prevent the moving or deforming object from escaping the field of view of the camera. In various embodiments, the camera zoom may be readjusted based on a direction and a speed of the moving or deforming object.

Figure 2:
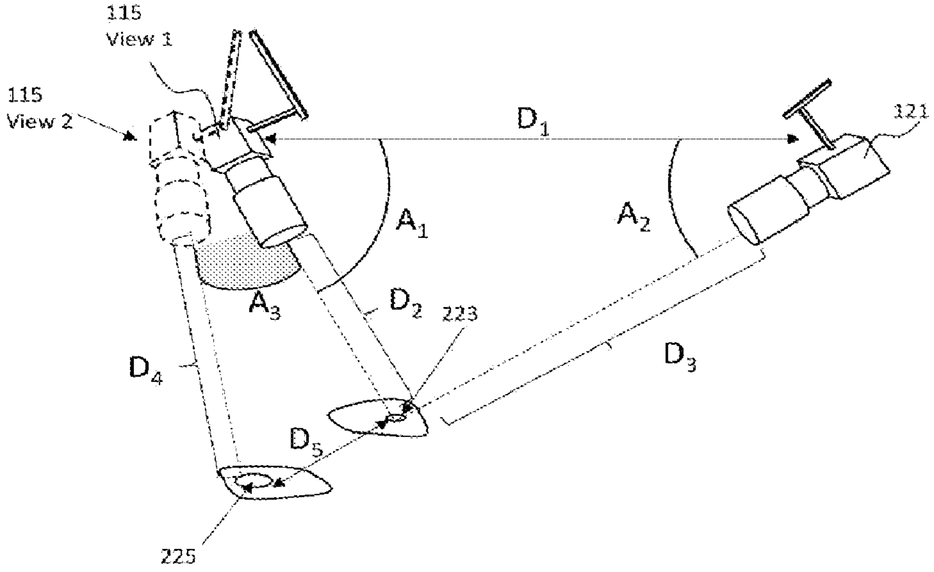
FIG. 2 is a perspective view of an exemplary camera arrangement, consistent with disclosed embodiments.

In various embodiments, one or more image sensors may include moving cameras 115, 121, 123 and 125. Cameras 115, 121, 123 and 125 may be used for determining sizes of anatomical structures and determining distances between different ROIs, for example using triangulation. For example, FIG. 2 shows exemplary cameras 115 (115 View 1, as shown in FIG. 2) and 121 supported by movable elements such that the distance between the two cameras is D1, as shown in FIG. 2. Both cameras point at ROI 223. By knowing the positions of cameras 115 and 121 and the direction of an object relative to the cameras (e.g., by knowing angles A1 and A2, as shown in FIG. 2, for example based on correspondences between pixels depicting the same object or the same real-world point in the images captured by 115 and 121), distances D2 and D3 may be calculated using, for example, the law of sines and the known distance between the two cameras D1. In an example embodiment, when camera 115 (115, View 2) rotates by a small angle A3 (measured in radians), to point at ROI 225, the distance between ROI 223 and ROI 225 may be approximated (for small angles A3) by A3D2. More accuracy may be obtained using another triangulation process. Knowing distances between ROI 223 and 225 allows determining a length scale for an anatomical structure. Further, distances between various points of the anatomical structure, and distances from the various points to one or more cameras may be measured to determine a point-cloud representing a surface of the anatomical structure. Such a point-cloud may be used to reconstruct a three-dimensional model of the anatomical structure. Further, distances between one or more surgical instruments and different points of the anatomical structure may be measured to determine proper locations of the one or more surgical instruments in the proximity of the anatomical structure. In some other examples, one or more of cameras 115, 121, 123 and 125 may include a 3D camera (such as a stereo camera, an active stereo camera, a Time of Flight camera, a Light Detector and Ranging camera, etc.), and actual and/or relative locations and/or sizes of objects within operating room 101, and/or actual distances between objects, may be determined based on the 3D information captured by the 3D camera.

Returning to FIG. 1, light sources (e.g., light source 119) may also be movable to track one or more ROIs. In an example embodiment, light source 119 may be rotated by yaw and pitch angles, and in some cases, may extend towards to or away from a ROI (e.g., location 127). In some cases, light source 119 may include one or more optical elements (e.g., lenses, flat or curved mirrors, and the like) to focus light on the ROI. In some cases, light source 119 may be configured to control the color of the light (e.g., the color of the light may include different types of white light, a light with a selected spectrum, and the like). In an example embodiment, light 119 may be configured such that the spectrum and intensity of the light may vary over a surface of an anatomic structure illuminated by the light. For example, in some cases, light 119 may include infrared wavelengths which may result in warming of at least some portions of the surface of the anatomic structure.

In some embodiments, the operating room may include sensors embedded in various components depicted or not depicted in FIG. 1. Examples of such sensors may include: audio sensors; image sensors; motion sensors; positioning sensors; chemical sensors; temperature sensors; barometers; pressure sensors; proximity sensors; electrical impedance sensors; electrical voltage sensors; electrical current sensors; or any other detector capable of providing feedback on the environment or a surgical procedure, including, for example, any kind of medical or physiological sensor configured to monitor patient 143.

In some embodiments, the operating room may include a wireless transmitter 145, capable of transmitting a location identifier, as illustrated in FIG. 1. The wireless transmitter may communicate with other elements in the operating room through wireless signals, such as radio communication including Bluetooth or Wireless USB, Wi-Fi, LPWAN, RFID, or other suitable wireless communication methods. In some embodiments, wireless transmitter 145 may be a receiver or transceiver. Accordingly, wireless transmitter 145 may be configured to receive signals for the purpose of determining a location of elements in the operating room. Although FIG. 1 depicts only one wireless transmitter 145, embodiments may include additional wireless transmitters. For example, a wireless transmitter may be associated with a particular patient, a particular doctor, an operating room, a piece of equipment, or any other object, place, or person. Wireless transmitter 145 may be attached to equipment, a room, or a person. For example, wireless transmitter 145 may be a wearable device or a component of a wearable device. In some embodiments, wireless transmitter 145 may be mounted to a wall or a ceiling. Generally, wireless transmitter 145 may be a standalone device or may be a component of device. For example, wireless transmitter 145 may be a component of a piece of medical equipment, a camera, a personal mobile device, or another system associated with a surgery. Additionally or alternatively, wireless transmitter 145 may be an active or a passive wireless tag, a wireless location beacon, and so forth.

In some embodiments, audio sensor 111 may include one or more audio sensors configured to capture audio by converting sounds to digital information (e.g., audio sensors 121).

In various embodiments, temperature sensors may include infrared cameras (e.g., an infrared camera 117 is shown in FIG. 1) for thermal imaging. Infrared camera 117 may allow measurements of the surface temperature of an anatomic structure at different points of the structure. Similar to visible cameras D115, 121, 123 and 125, infrared camera 117 may be rotated using yaw or pitch angles. Additionally or alternatively, camera 117 may include an image sensor configured to capture image from any light spectrum, include infrared image sensor, hyper-spectral image sensors, and so forth.

FIG. 1 includes a display screen 113 that may show views from different cameras 115, 121, 123 and 125, as well as other information. For example, display screen 113 may show a zoomed-in image of a tip of a surgical instrument and a surrounding tissue of an anatomical structure in proximity to the surgical instrument.

Figure 3:
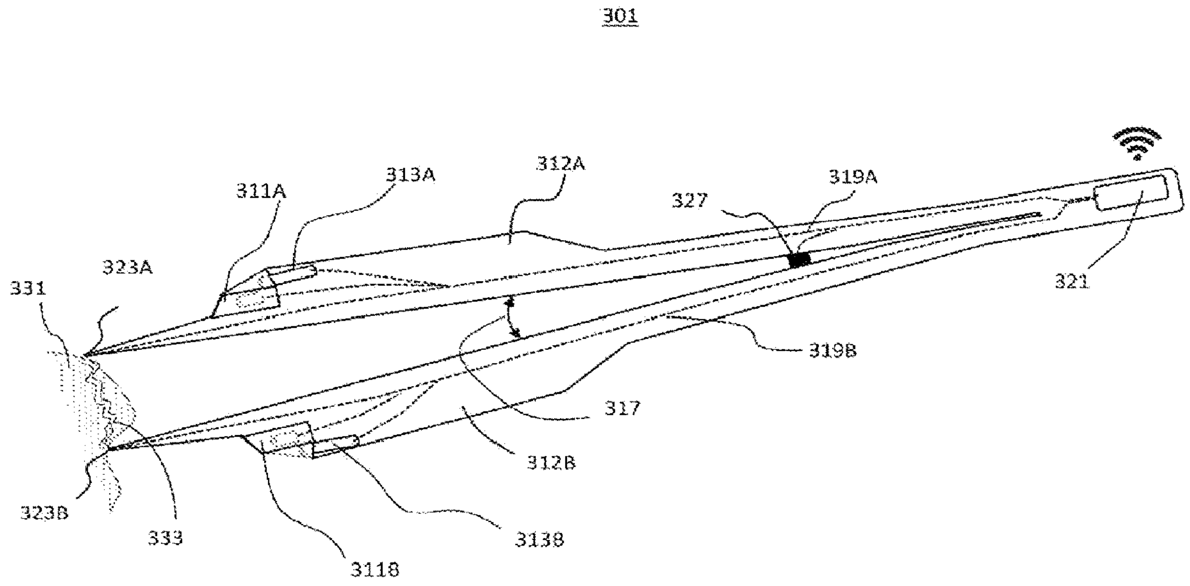
FIG. 3 is a perspective view of an example of a surgical instrument, that may be used in connection with disclosed embodiments.

FIG. 3 shows an example embodiment of a surgical instrument 301 that may include multiple sensors and light-emitting sources. Consistent with the present embodiments, a surgical instrument may refer to a medical device, a medical instrument, an electrical or mechanical tool, a surgical tool, a diagnostic tool, and/or any other instrumentality that may be used during a surgery. As shown, instrument 301 may include cameras 311A and 311B, light sources 313A and 313B as well as tips 323A and 323B for contacting tissue 331. Cameras 311A and 311B may be connected via data connection 319A and 319B to a data transmitting device 321. In an example embodiment, device 321 may transmit data to a data-receiving device using a wireless communication or using a wired communication. In an example embodiment, device 321 may use WiFi, Bluetooth, NFC communication, inductive communication, or any other suitable wireless communication for transmitting data to a data-receiving device. The data-receiving device may include any form of receiver capable of receiving data transmissions. Additionally or alternatively, device 321 may use optical signals to transmit data to the data-receiving device (e.g., device 321 may use optical signals transmitted through the air or via optical fiber). In some embodiments, device 301 may include local memory for storing at least some of the data received from sensors 311A and 311B. Additionally, device 301 may include a processor for compressing video/image data before transmitting the data to the data-receiving device.

In various embodiments, for example when device 301 is wireless, it may include an internal power source (e.g., a battery, a rechargeable battery, and the like) and/or a port for recharging the battery, an indicator for indicating the amount of power remaining for the power source, and one or more input controls (e.g., buttons) for controlling the operation of device 301. In some embodiments, control of device 301 may be accomplished using an external device (e.g., a smartphone, tablet, smart glasses) communicating with device 301 via any suitable connection (e.g., WiFi, Bluetooth, and the like). In an example embodiment, input controls for device 301 may be used to control various parameters of sensors or light sources. For example, input controls may be used to dim/brighten light sources 313A and 313B, move the light sources for cases when the light sources may be moved (e.g., the light sources may be rotated using yaw and pitch angles), control the color of the light sources, control the focusing of the light sources, control the motion of cameras 311A and 311B for cases when the cameras may be moved (e.g., the cameras may be rotated using yaw and pitch angles), control the zoom and/or capturing parameters for cameras 311A and 311B, or change any other suitable parameters of cameras 311A-311B and light sources 313A-313B. It should be noted camera 311A may have a first set of parameters and camera 311B may have a second set of parameters that is different from the first set of parameters, and these parameters may be selected using appropriate input controls. Similarly, light source 313A may have a first set of parameters and light source 313B may have a second set of parameters that is different from the first set of parameters, and these parameters may be selected using appropriate input controls.

Additionally, instrument 301 may be configured to measure data related to various properties of tissue 331 via tips 323A and 323B and transmit the measured data to device 321. For example, tips 323A and 323B may be used to measure the electrical resistance and/or impedance of tissue 331, the temperature of tissue 331, mechanical properties of tissue 331 and the like. To determine elastic properties of tissue 331, for example, tips 323A and 323B may be first separated by an angle 317 and applied to tissue 331. The tips may be configured to move such as to reduce angle 317, and the motion of tips may result in pressure on tissue 331. Such pressure may be measured (e.g., via a piezoelectric element 327 that may be located between a first branch 312A and a second branch 312B of instrument 301), and based on the change in angle 317 (i.e., strain) and the measured pressure (i.e., stress), the elastic properties of tissue 331 may be measured. Furthermore, based on angle 317 distance between tips 323A and 323B may be measured, and this distance may be transmitted to device 321. Such distance measurements may be used as a length scale for various video/image data that may be captured by various cameras 115, 121, 123 and 125, as shown in FIG. 1.

Instrument 301 is only one example of possible surgical instrument, and other surgical instruments such as scalpels, graspers (e.g., forceps), clamps and occluders, needles, retractors, cutters, dilators, suction tips, and tubes, sealing devices, irrigation and injection needles, scopes and probes, and the like, may include any suitable sensors and light-emitting sources. In various cases, the type of sensors and light-emitting sources may depend on a type of surgical instrument used for a surgical procedure. In various cases, these other surgical instruments may include a device similar to device 301, as shown in FIG. 3, for collecting and transmitting data to any suitable data-receiving device.

Aspects of the present disclosure may involve medical professionals performing surgical procedures. A medical professional may include, for example, a surgeon, a surgical technician, a resident, a nurse, a physician's assistant, an anesthesiologist, a doctor, a veterinarian surgeon, and so forth. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal, or may include veterinarian surgeries. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopie procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

Aspects of this disclosure may relate to using machine learning to solve problems in the field of video processing. For example, aspects of this disclosure provide solutions for detecting events otherwise undetectable by a human, and in some examples, to create new data structures which may be indexable, searchable, and efficiently organized across a wide variety of platforms and multiple devices.

Aspects of this disclosure may relate to statistical analysis operations. Statistical analysis operations may include collecting, organizing, analyzing, interpreting, or presenting data. Statistical analysis may include data analysis or data processing.

For ease of discussion, a method is described below with the understanding that aspects of the method apply equally to systems, devices, and computer readable media. For example, some aspects of such a method may occur electronically over a network that may be either wired, wireless, or both. Other aspects of such a method may occur using non-electronic means. In a broadest sense, the method is not limited to particular physical and/or electronic instrumentalities, but rather may be accomplished using many differing instrumentalities.

Disclosed embodiments may involve receiving a plurality of video frames from a plurality of surgical videos. Surgical videos may refer to any video, group of video frames, or video footage including representations of a surgical procedure. For example, the surgical video may include one or more video frames captured during a surgical operation. In another example, the surgical video may include one or more video frames captured from within a surgical cavity, for example using a camera positioned the body of the patient. A plurality of video frames may refer to a grouping of frames from one or more surgical videos or surgical video clips. The video frames may be stored in a common location or may be stored in a plurality of differing storage locations. Although not necessarily so, video frames within a received group may be related in some way. For example, video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics. Alternatively, one or more video frames may be captured at different times from surgical procedures performed on differing patients.

The plurality of sets of surgical video footage may reflect a plurality of surgical procedures performed by a specific medical professional. A specific medical professional may include, for example, a specific surgeon, a specific surgical technician, a specific resident, a specific nurse, a specific physician's assistant, a specific anesthesiologist, a specific doctor, a specific veterinarian surgeon, and so forth. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

A surgical procedure may be performed by a specific medical professional, such as a surgeon, a surgical technician, a resident, a nurse, a physician's assistant, an anesthesiologist, a doctor, a veterinarian surgeon, or any other healthcare professional. It is often desirable to track performance of a specific medical professional over a wide range of time periods or procedures, but such analysis may be difficult because often no record exists of performance, and even when video is captured, meaningful analysis over time is typically not humanly possible. This is due to the fact that surgical procedures tend to be extended in time, with portions of interest from an analytical perspective being buried within high volumes of extraneous frames. It would be unworkable for a human to review hours of video, identifying and isolating similar frames from differing surgical procedures, let alone performing meaningful comparative analysis. Accordingly, disclosed embodiments enable analysis of surgical events or surgical outcomes related to specific medical professionals. A medical professional may have one or more of a number of characteristics, such as an age, a sex, an experience level, a skill level, or any other measurable characteristic. The specific medical professional may be identified automatically using computer image analysis, such as facial recognition or other biometric recognition methods. Alternatively or additionally, the specific medical professional may be identified using metadata, tags, labels, or other classification information associated with videos or contained in an associated electronic medical record. In some embodiments, the specific medical professional may be identified based on user input and/or a database containing identification information related to medical professionals.

The plurality of surgical video frames may be associated with differing patients. For example, a number of different patients who underwent the same or similar surgical procedure, or who underwent surgical procedures where a similar technique was employed may be included within a common set or a plurality of sets. Alternatively or in addition, one or more sets may include surgical footage captured from a single patient but at different times or from different image capture devices. The plurality of surgical procedures may be of the same type, for example, all including appendectomies, or may be of different types. In some embodiments, the plurality of surgical procedures may share common characteristics, such as the same or similar phases or intraoperative events. As referred to in this paragraph, each video of the plurality of surgical videos may be associated with a differing patient. That is, if the plurality may include only two videos, each video may be from a differing patient. If the plurality of videos includes more than two videos, it is sufficient that videos reflect surgical procedures performed on at least two differing patients.

Some aspects of the present disclosure may involve accessing a set of surgical event-related categories, wherein each surgical event-related category may be denoted by a differing category indicator. A surgical event-related category may include any classification or label associated with the surgical event. Some non-limiting examples of such categories may include a procedure step, a safety milestone, a point of decision, an intraoperative event, an operative milestone or an intraoperative decision. A surgical event-related category indicator may include any sign, pointer, tag, or code identifying a surgical event-related category. In one sense, the category indicator may be the full name of, or an abbreviation of the category. In other embodiments, the category indicator may be a code or tag mapped to the surgical event or an occurrence within the surgical event. Surgical event-related category indicators may be stored in a database or data structure. By storing or using surgical event-related category indicators, disclosed embodiments solve problems in the field of statistical analysis by creating standardized uniform classification labels for data points, allowing data to be structured and stored in systematic and organized ways to improve efficiency and accuracy in data analysis.

In some embodiments, analyzing the received video frames of each surgical video may include identifying surgical events in each of a plurality of surgical videos. Identification of a plurality of surgical events in each of the plurality of surgical videos may include performing computer image analysis on frames of the video footage to identify at least one surgical event, such as a procedure step, a safety milestone, a point of decision, an intraoperative event, an operative milestone, or an intraoperative decision. For example, analyzing the received plurality of video frames may include identifying an incision, a fluid leak, excessive bleeding, or any other surgical event. Identified surgical events in surgical videos may defined by differing subgroup of frames. Alternatively or additionally, the identified plurality of surgical events may include overlapping subgroups of frames (e.g., two subgroups may share at least one common frame). For example, a subgroup of frames may relate to a surgical action, such as an incision procedure, and an overlapping subgroup of frames to an adverse event such as a fluid leakage event. Analyzing the received video frames to identify surgical events may involve any form of electronic analysis using a computing device including computer image analysis and artificial intelligence.

Some aspects of the present disclosure may include assigning each differing subgroup of frames to one of the surgical event-related categories to thereby interrelate subgroups of frames from differing surgical procedures under an associated common surgical event-related category. Any suitable means may be used to assign the subgroup of frames to one of the surgical event-related categories. Assignment of a subgroup of frames to one of the surgical event-related categories may occur through manual user input or through computer image analysis trained using a neural network model or other trained machine learning algorithm.

In some examples, subgroups of frames from differing surgical procedures may be assigned to common surgical event-related categories through computer image analysis trained with a machine learning algorithm. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

Assignment of a subgroup of frames may generate tags or labels associated with the frames. For example, tags may correspond to differing surgical event-related categories, such as a procedure step, a safety milestone, a point of decision, an intraoperative event, an operative milestone, or an intraoperative decision. Tags may include a timestamp, time range, frame number, or other means for associating the surgical event-related category to the subgroup of frames. In other embodiments, the tag may be associated with the subgroup of frames in a database. For example, the database may include information linking the surgical event-related category to the video frames and to the particular video footage location. The database may include a data structure, as described in further detail herein.

Figure 4:
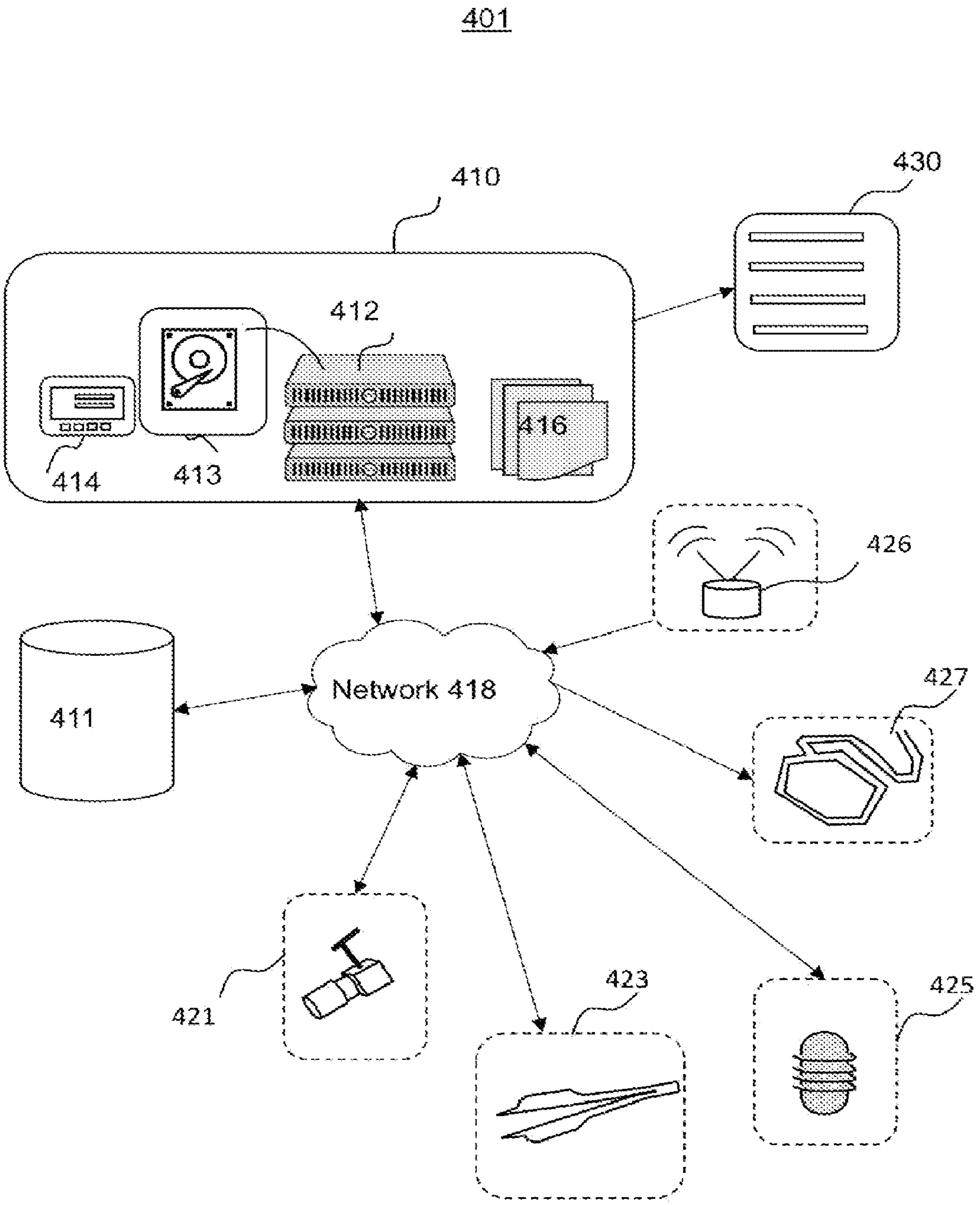
FIG. 4 is a network diagram of an exemplary system for managing various data collected during a surgical procedure, and for controlling various sensors consistent with disclosed embodiments.

Accessing the video of the surgical procedure may be performed via communication to a computer system through a network. For example, FIG. 4 shows an example system 401 that may include a computer system 410, a network 418, and image sensors 421 (e.g., cameras positioned within the operating room), and 423 (e.g., image sensors being part of a surgical instrument) connected via network 418 to computer system 401. System 401 may include a database 411 for storing various types of data related to previously conducted surgeries (i.e., historical surgical data that may include historical image, video or audio data, text data, doctors' notes, data obtained by analyzing historical surgical data, and other data relating to historical surgeries). In various embodiments, historical surgical data may be any surgical data related to previously conducted surgical procedures. Additionally, system 401 may include one or more audio sensors 425, wireless transmitters 426, light emitting devices 427, and a schedule 430.

Computer system 410 may include one or more processors 412 for analyzing the visual data collected by the image sensors, a data storage 413 for storing the visual data and/or other types of information, an input module 414 for entering any suitable input for computer system 410, and software instructions 416 for controlling various aspects of operations of computer system 410.

One or more processors 412 of system 410 may include multiple core processors to handle concurrently multiple operations and/or streams. For example, processors 412 may be parallel processing units to concurrently handle visual data from different image sensors 421 and 423. In some embodiments, processors 412 may include one or more processing devices, such as, but not limited to, microprocessors from the Pentium™ or Xeon™ family manufactured by Intel™, the Turion™ family manufactured by AMD™, or any of various processors from other manufacturers. Processors 412 may include a plurality of co-processors, each configured to run specific operations such as floating-point arithmetic, graphics, signal processing, string processing, or I/O interfacing. In some embodiments, processors may include a field-programmable gate array (FPGA), central processing units (CPUs), graphical processing units (GPUs), and the like.

Database 411 may include one or more computing devices configured with appropriate software to perform operations for providing content to system 410. Database 411 may include, for example, Oracle™ database, Sybase™ database, and/or other relational databases or non-relational databases, such as Hadoop™ sequence files, HBase™, or Cassandra™. In an illustrative embodiment, database 411 may include computing components (e.g., database management system, database server, etc.) configured to receive and process requests for data stored in memory devices of the database and to provide data from the database. As discussed before, database 411 may be configured to collect and/or maintain the data associated with surgical procedures. Database 411 may collect the data from a variety of sources, including, for instance, online resources.

Network 418 may include any type of connections between various computing components. For example, network 418 may facilitate the exchange of information via network connections that may include Internet connections, Local Area Network connections, near field communication (NFC), and/or other suitable connection(s) that enables the sending and receiving of information between the components of system 401. In some embodiments, one or more components of system 401 may communicate directly through one or more dedicated communication links.

Various example embodiments of the system 401 may include computer-implemented methods, tangible non-transitory computer-readable mediums, and systems. The computer-implemented methods may be executed, for example, by at least one processor that receives instructions from a non-transitory computer-readable storage medium such as medium 413, as shown in FIG. 4. Similarly, systems and devices consistent with the present disclosure may include at least one processor and memory, and the memory may be a non-transitory computer-readable storage medium. As used herein, a non-transitory computer-readable storage medium refers to any type of physical memory on which information or data readable by at least one processor can be stored. Examples may include random access memory (RAM), read-only memory (ROM), volatile memory, non-volatile memory, hard drives, CD ROMs, DVDs, flash drives, disks, and any other known physical storage medium whether some or all portions thereof are physically located in or near the operating room, in another room of the same facility, at a remote captive site, or in a cloud-based server farm. Singular terms, such as "memory" and "computer-readable storage medium." may additionally refer to multiple structures, such a plurality of memories or computer-readable storage mediums. As referred to herein, a "memory" may include any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Input module 414 may be any suitable input interface for providing input to one or more processors 412. In an example embodiment, input interface may be a keyboard for inputting alphanumerical characters, a mouse, a joystick, a touch screen, an on-screen keyboard, a smartphone, an audio capturing device (e.g., a microphone), a gesture capturing device (e.g., camera), and other device for inputting data. While a user inputs the information, the information may be displayed on a monitor to ensure the correctness of the input. In various embodiments, the input may be analyzed verified or changed before being submitted to system 410.

Software instructions 416 may be configured to control various aspects of operation of system 410, which may include receiving and analyzing the visual data from the image sensors, controlling various aspects of the image sensors (e.g., moving image sensors, rotating image sensors, operating zoom lens of image sensors for zooming towards an example ROI, and/or other movements), controlling various aspects of other devices in the operating room (e.g., controlling operation of audio sensors, chemical sensors, light emitting devices, and/or other devices).

As previously described, image sensors 421 may be any suitable sensors capable of capturing image or video data. For example, such sensors may be cameras 115-125.

Audio sensors 425 may be any suitable sensors for capturing audio data. Audio sensors 425 may be configured to capture audio by converting sounds to digital information. Some examples of audio sensors 425 may include microphones, unidirectional microphones, bidirectional microphones, cardioid microphones, omnidirectional microphones, onboard microphones, wired microphones, wireless microphones, any combination of the above, and any other sound-capturing device.

Wireless transmitter 426 may include and suitable wireless device capable of transmitting a location identifier. The wireless transmitter may communicate with other elements in the operating room through wireless signals, such as radio communication including Bluetooth or Wireless USB, Wi-Fi, LPWAN, or other suitable wireless communication methods.

Light emitting devices 427 may be configured to emit light, for example, in order to enable better image capturing by image sensors 421. In some embodiments, the emission of light may be coordinated with the capturing operation of image sensors 421. Additionally or alternatively, the emission of light may be continuous. In some cases, the emission of light may be performed at selected times. The emitted light may be visible light, infrared light, ultraviolet light, deep ultraviolet light, x-rays, gamma rays, and/or in any other portion of the light spectrum.

Aspects of this disclosure may relate to detecting surgical instruments. A surgical instrument may refer to a medical device, a medical instrument, an electrical or mechanical tool, a surgical tool, a diagnostic tool, and/or any other instrumentality that may be used during a surgery such as scalpels, graspers (e.g., forceps), clamps and occluders, needles, retractors, cutters, dilators, suction tips, and tubes, scaling devices, irrigation and injection needles, scopes and probes, and the like. By way of one example, a surgical instrument may include instrument 301 shown in FIG. 3.

Some aspects of the present disclosure may involve accessing stored data. Stored data may refer to data of any format that was recorded and/or stored previously. In some embodiments, the stored data may be one or more video files including historical surgical footage. For example, the stored data may include a series of frames captured during the prior surgical procedures. This stored data is not limited to video files, however. For example, the stored data may include information stored as text representing at least one aspect of the stored surgical footage. For example, the stored data may include a database of information summarizing or otherwise referring to historical surgical footage. In another example, the stored data may include information stored as numerical values representing at least one aspect of the historical surgical footage. In an additional example, the stored data may include statistical information and/or statistical model based on an analysis of the historical surgical footage. In yet another example, the stored data may include a machine learning model trained using training examples, and the training examples may be based on the historical surgical footage. Accessing the stored data may include receiving the stored data through an electronic transmission, retrieving the historical data from storage (e.g., a memory device), or any other process for accessing data. In some embodiments, the stored data may be accessed from the same resource as the particular surgical footage discussed above. In other embodiments, the stored data may be accessed from a separate resource. Additionally or alternatively, accessing the stored data may include generating the stored data, for example by analyzing previously recorded surgical procedures or by analyzing data based on the stored surgical footage of prior surgical procedures.

In an example embodiment, the data structure may be a relational database having one or more database tables. For instance, FIG. 5 illustrates an example of data structure 501 that may include data tables 511 and 513. In an example embodiment, data structure 501 may be part of relational databases, may be stored in memory, and so forth. Tables 511 and 513 may include multiple records (e.g., records 1 and 2, as shown in FIG. 5) and may have various fields, such as fields "Record Number", "Procedure", "Age", "Gender", "Medical Considerations", "Time", and "Other Data". For instance, field "Record Number" may include a label for a record that may be an integer, field "Procedure" may include a name of a surgical procedure, field "Age" may include an age of a patient, field "Gender" may include a gender of the patient, field "Medical Considerations" may include information about medical history for the patient that may be relevant to the surgical procedure having the name as indicated in field "Procedure", field "Time" may include time that it took for the surgical procedure, and field "Other Data" may include links to any other suitable data related to the surgical procedure. For example, as shown in FIG. 5, 511 may include links to data 512A that may correspond to image data, data 512B that may correspond to video data, data 512C that may correspond to text data (e.g., notes recorded during or after the surgical procedure, patient records, postoperative report, etc.), and data 512D that may correspond to an audio data. In various embodiments, image, video, or audio data may be captured during the surgical procedure. In some cases, video data may also include audio data. Image, video, text or audio data 512A-512D are only some of the data that may be collected during the surgical procedure. Other data may include vital sign data of the patient, such as heart rate data, blood pressure data, blood test data, oxygen level, or any other patient-related data recorded during the surgical procedure. Some additional examples of data may include room temperature, type of surgical instruments used, or any other data related to the surgical procedure and recorded before, during or after the surgical procedure.

As shown in FIG. 5, tables 511 and 513 may include a record for a surgical procedure. For example, tables may have information about surgical procedures, such as the type of procedure, patient information or characteristics, length of the procedure, a location of the procedure, a surgeon's identify or other information, an associated anesthesiologist's identity, the time of day of the surgical procedure, whether the surgical procedure was a first, a second, a third, etc. procedure conducted by a surgeon (e.g., in the surgeon lifetime, within a particular day, on a particular patient, etc.), an associated anesthesiologist nurse assistant, whether there were any complications during the surgical procedure, and any other information relevant to the procedure. For example, record 1 of table 511 indicates that a bypass surgical procedure was performed on a male of 65 years old, having a renal disease and that the bypass surgery was completed in 4 hours. A record 2 of table 511 indicates that a bypass surgical procedure was performed on a female of 78 years old, having no background medical condition that may complicate the surgical procedure, and that the bypass surgery was completed in 3 hours. Table 513 indicates that the bypass surgery for the male of 65 years old was conducted by Dr. Mac, and that the bypass surgery for the female of 78 years old was conducted by Dr. Doc. The patient characteristics such as age, gender, and medical considerations listed in table 511 are only some of the example patient characteristics, and any other suitable characteristics may be used to differentiate one surgical procedure from another. For example, patient characteristics may further include patient allergies, patient tolerance to anesthetics, various particulars of a patient (e.g., how many arteries need to be treated during the bypass surgery), a weight of the patient, a size of the patient, particulars of anatomy of the patient, or any other patient related characteristics which may have an impact on a duration (and success) of the surgical procedure.

Data structure 501 may have any other number of suitable tables that may characterize any suitable aspects of the surgical procedure. For example, 501 may include a table indicating an associated anesthesiologist's identity, the time of day of the surgical procedure, whether the surgical procedure was a first, a second, a third, etc. procedure conducted by a surgeon (e.g., in the surgeon lifetime, within a particular day, etc.), an associated anesthesiologist nurse assistant, whether there were any complications during the surgical procedure, and any other information relevant to the procedure.

Accessing a data structure may include reading and/or writing information to the data structure. For example, reading and/or writing from/to the data structure may include reading and/or writing any suitable historical surgical data such as historic visual data, historic audio data, historic text data (e.g., notes during an example historic surgical procedure), and/or other historical data formats. In an example embodiment, accessing the data structure may include reading and/or writing data from/to database 111 or any other suitable electronic storage repository. In some cases, writing data may include printing data (e.g., printing reports containing historical data on paper).

FIG. 6 illustrates an example data structure 600 consistent with the disclosed embodiments. As shown in FIG. 6, data structure 600 may comprise a table including video footage 610 and video footage 620 pertaining to different surgical procedures. For example, video footage 610 may include footage of a laparoscopic cholecystectomy, while video footage 620 may include footage of a cataract surgery. Video footage 620 may be associated with footage location 621, which may correspond to a particular surgical phase of the cataract surgery. Phase tag 622 may identify the phase (in this instance a corneal incision) associated with footage location 621, as discussed above. Video footage 620 may also be associated with event tag 624, which may identify an intraoperative surgical event (in this instance an incision) within the surgical phase occurring at event location 623. Video footage 620 may further be associated with event characteristic 625, which may describe one or more characteristics of the intraoperative surgical event, such as surgeon skill level, as described in detail above. Each video footage identified in the data structure may be associated with more than one footage location, phase tag, event location, event tag and/or event characteristic. For example, video footage 610 may be associated with phase tags corresponding to more than one surgical phase (e.g., "Calot's triangle dissection" and "cutting of cystic duct"). Further, each surgical phase of a particular video footage may be associated with more than one event, and accordingly may be associated with more than one event location, event tag, and/or event characteristic. It is understood, however, that in some embodiments, a particular video footage may be associated with a single surgical phase and/or event. It is also understood that in some embodiments, an event may be associated with any number of event characteristics, including no event characteristics, a single event characteristic, two event characteristics, more than two event characteristics, and so forth. Some non-limiting examples of such event characteristics may include skill level associated with the event (such as minimal skill level required, skill level demonstrated, skill level of a medical care giver involved in the event, etc.), time associated with the event (such as start time, end time, etc.), type of the event, information related to medical instruments involved in the event, information related to anatomical structures involved in the event, information related to medical outcome associated with the event, one or more amounts (such as an amount of leak, amount of medication, amount of fluids, etc.), one or more dimensions (such as dimensions of anatomical structures, dimensions of incision, etc.), and so forth. Further, it is to be understood that data structure 600 is provided by way of example and various other data structures may be used.

Correct performance of surgical procedures, including the performance of the different steps of a surgical procedure in the right time and order, depends on the surgeon performing the surgical procedure. While surgeons are highly skilled and trained to avoid errors, errors do occur, as in any other human activity. While the training reduces the number of errors, the errors that do occur in a surgical procedure may have dire consequences. Having a peer or a supervisor in the operating room while the surgical procedure is ongoing to warn before an action is about to take place at an unsuitable phase of the ongoing surgical procedure may reduce the number of errors. This is a common solution when training new surgeons. However, the time and effort required from the peers and supervisors to oversee all surgeries, even of senior surgeons, will be enormous. Therefore, it is beneficial to have an automated detection of prospective adverse actions in surgical procedures.

Systems, methods, and non-transitory computer readable media for detecting prospective adverse actions in surgical procedures are provided. For example, a system for detecting prospective adverse actions in surgical procedures may include at least one processor, as described above, and the processor may be configured to perform the steps of process 700. In another example, a computer readable medium for detecting prospective adverse actions in surgical procedures, such as a non-transitory computer readable medium, may store data and/or computer implementable instructions that, when executed by at least one processor, causes the at least one processor to perform operations for carrying out the steps of process 700. In other examples, the steps of process 700 may be carried out by any means.

Figure 7:
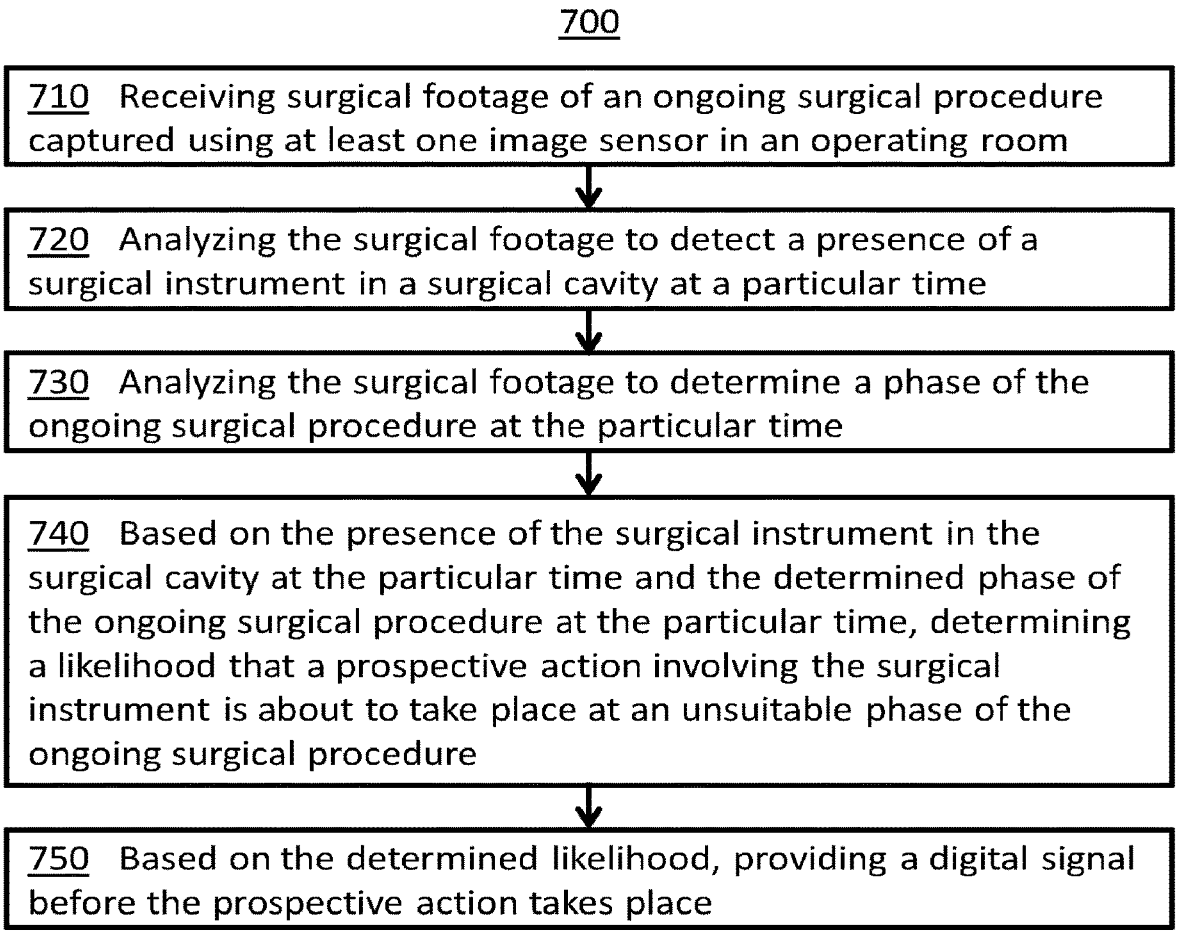
FIG. 7 is a flowchart illustrating an exemplary process for detecting prospective adverse actions in surgical procedures, consistent with disclosed embodiments.

FIG. 7 is a flowchart illustrating an exemplary process 700 for detecting prospective adverse actions in surgical procedures, consistent with disclosed embodiments. In this example, process 700 may comprise: receiving surgical footage of an ongoing surgical procedure captured using at least one image sensor in an operating room (Step 710); analyzing the surgical footage to detect a presence of a surgical instrument in a surgical cavity at a particular time (Step 720); analyzing the surgical footage to determine a phase of the ongoing surgical procedure at the particular time (Step 730); based on the presence of the surgical instrument in the surgical cavity at the particular time and the determined phase of the ongoing surgical procedure at the particular time, determining a likelihood that a prospective action involving the surgical instrument is about to take place at an unsuitable phase of the ongoing surgical procedure (Step 740); and, based on the determined likelihood, providing a digital signal before the prospective action takes place (Step 750).

In some embodiments, Step 710 may comprise receiving surgical footage of an ongoing surgical procedure captured using at least one image sensor in an operating room. For example, the received surgical footage of the ongoing surgical procedure may include surgical footage captured using at least one of overhead camera 115, overhead camera 121, overhead camera 123, tableside camera 125 or image sensors 421. In some examples, receiving surgical footage by Step 710 may include reading the surgical footage from memory. In some examples, receiving surgical footage by Step 710 may include receiving the surgical footage from an external device, for example using a digital communication device via a digital communication line or a digital communication network. In some examples, receiving surgical footage by Step 710 may include capturing the surgical footage using the at least one image sensor.

In some embodiments, Step 720 may comprise analyzing a surgical footage (such as the surgical footage received by Step 710) to detect a presence of a surgical instrument in a surgical cavity at a particular time. For example, Step 720 may use an object detection algorithm to analyze the surgical footage received by Step 710 to detect the surgical instrument in the surgical cavity at one or more frames corresponding to the particular time. In another example, a machine learning model may be trained using training examples to detect surgical instruments in surgical cavities in images and/or videos. An example of such training example may include a sample image or sample video, together with a label indicating whether the sample image or sample video depicts a surgical instrument in a surgical cavity. Step 720 may use the trained machine learning model to analyze the surgical footage received by Step 710 to detect the surgical instrument in the surgical cavity at one or more frames corresponding to the particular time. In some examples, Step 720 may analyze at least part of the surgical footage received by Step 710 to calculate a convolution of the at least part of the surgical footage received by Step 710 and thereby obtain a result value of the calculated convolution. Further, in response to the result value of the calculated convolution being a first value, Step 720 may detect the surgical instrument in the surgical cavity, and in response to the result value of the calculated convolution being a second value, Step 720 may avoid detecting the surgical instrument in the surgical cavity. In some examples, the surgical instrument may include a particular text on its surface, and Step 720 may use an Optical Character Recognition (OCR) algorithm to analyze at least part of the surgical footage received by Step 710 to detect the particular text and thereby the surgical instrument. In some examples, the surgical instrument may include a particular visual code (such as a barcode or QR code) on its surface, and Step 720 may use a visual detection algorithm to analyze at least part of the surgical footage received by Step 710 to detect the particular visual code and thereby the surgical instrument.

In some embodiments, Step 730 may comprise analyzing a surgical footage (such as the surgical footage received by Step 710) to determine a phase of the ongoing surgical procedure at the particular time. For example, a machine learning model may be trained using training examples to determine phases of surgical procedures from images and/or videos. An example of such training example may include a sample image or a sample video captured at a specific time in a sample surgical procedure, together with a label indicating a phase of the sample surgical procedure corresponding to the specific time. Step 730 may use the trained machine learning model to analyze at least part of the surgical footage received by Step 710 to determine the phase of the ongoing surgical procedure at the particular time. In some examples, Step 730 may analyze at least part of the surgical footage received by Step 710 to calculate a convolution of the at least part of the surgical footage received by Step 710 and thereby obtain a result value of the calculated convolution. Further, in response to the result value of the calculated convolution being a first value, Step 730 may determine that the phase of the ongoing surgical procedure at the particular time is one phase, and in response to the result value of the calculated convolution being a second value, Step 730 may determine that the phase of the ongoing surgical procedure at the particular time is a different phase. In some examples, different phases may be associated with different surgical actions, and Step 730 may use a visual action recognition algorithm to analyze at least part of the surgical footage received by Step 710 to detect a particular surgical action. Further, Step 730 may access a data-structure to determine that the particular surgical action corresponds to a particular phase, and may determine that the phase of the ongoing surgical procedure at the particular time is the particular phase.

In some examples, surgical footage (such as the surgical footage received by Step 710) may be analyzed to determine that surgical instruments of a particular type were not used in the ongoing surgical procedure before the particular time. For example, a visual object recognition algorithm may be used to analyze the surgical footage and determine the types of the surgical instruments used in the ongoing surgical procedure before the particular time, and the particular type may be compared with the types of the surgical instruments used in the ongoing surgical procedure before the particular time to determine that surgical instruments of the particular type were not used in the ongoing surgical procedure before the particular time. In another example, a machine learning model may be trained using training examples to determine whether surgical instruments of the particular type were used from images and/or videos. An example of such training example may include a sample surgical image or video of a sample surgical procedure, together with a label indicating whether surgical instruments of the particular type were used. The trained machine learning model may be used to analyze the surgical footage and determine that surgical instruments of the particular type were not used in the ongoing surgical procedure before the particular time. In some examples, Step 730 may base the determination of the phase of the ongoing surgical procedure at the particular time on the determination that surgical instruments of the particular type were not used in the ongoing surgical procedure before the particular time. For example, when surgical instruments of the particular type were not used in the ongoing surgical procedure before the particular time, Step 730 may determine that the phase of the ongoing surgical procedure at the particular time is one phase, and when surgical instruments of the particular type were used in the ongoing surgical procedure before the particular time, Step 730 may determine that the phase of the ongoing surgical procedure at the particular time is another phase.

In some examples, surgical footage (such as the surgical footage received by Step 710) may be analyzed to determine that a particular action was not taken in the ongoing surgical procedure before the particular time. For example, a visual action recognition algorithm may be used to analyze the surgical footage and determine the actions taken in the ongoing surgical procedure before the particular time, and the particular action may be compared with the actions taken in the ongoing surgical procedure before the particular time to determine that the particular action was not taken in the ongoing surgical procedure before the particular time. In another example, a machine learning model may be trained using training examples to determine whether particular actions were taken in selected portions of surgical procedures from images and/or videos. An example of such training example may include a sample surgical image or video of a sample portion of a sample surgical procedure, together with a label indicating whether a particular action was taken in the sample portion of the sample surgical procedure. The trained machine learning model may be used to analyze the surgical footage and determine that the particular action was not taken in the ongoing surgical procedure before the particular time. In some examples, Step 730 may base the determination of the phase of the ongoing surgical procedure at the particular time on the determination that the particular action was not taken in the ongoing surgical procedure before the particular time. For example, when the particular action was not taken in the ongoing surgical procedure before the particular time, Step 730 may determine that the phase of the ongoing surgical procedure at the particular time is one phase, and when the particular action was taken in the ongoing surgical procedure before the particular time, Step 730 may determine that the phase of the ongoing surgical procedure at the particular time is another phase.

In some examples, surgical footage (such as the surgical footage received by Step 710) may be analyzed to determine a status of an anatomical structure at the particular time. For example, a visual classification algorithm may be used to analyze the surgical footage and classy the anatomical structure to one or a plurality of alternative classes, each alternative class may correspond to a status of the anatomical structure, and thereby the classification may determine the status of the anatomical structure at the particular time. In some examples, Step 730 may base the determination of the phase of the ongoing surgical procedure at the particular time on the status of the anatomical structure at the particular time. For example, when the status of the anatomical structure at the particular time is a first status, Step 730 may determine that the phase of the ongoing surgical procedure at the particular time is one phase, and when the status of the anatomical structure at the particular time is a second status, Step 730 may determine that the phase of the ongoing surgical procedure at the particular time is another phase.

In some examples, an indication of an elapsed time from a selected point in the ongoing surgical procedure to the particular time may be received. For example, receiving the indication may include reading the indication from memory. In another example, receiving the indication may include receiving the indication from an external device, for example using a digital communication device. In yet another example, receiving the indication may include calculating or measuring the elapsed time from the selected point in the ongoing surgical procedure to the particular time. For example, surgical footage (such as the surgical footage received by Step 710) may be analyzed to identify the selected point in the ongoing surgical procedure. In some examples, Step 730 may further base the determination of the phase of the ongoing surgical procedure at the particular time on the elapsed time. For example, when the elapsed time is in a first range, Step 730 may determine that the phase of the ongoing surgical procedure at the particular time is one phase, and when the elapsed time is in a second range, Step 730 may determine that the phase of the ongoing surgical procedure at the particular time is another phase.

In some embodiments, Step 740 may comprise, based on the presence of the surgical instrument in the surgical cavity at the particular time (detected by Step 720) and the phase of the ongoing surgical procedure at the particular time determined by Step 730, determining a likelihood that a prospective action involving the surgical instrument is about to take place at an unsuitable phase of the ongoing surgical procedure. In one example, the unsuitable phase of the ongoing surgical procedure is the phase of the ongoing surgical procedure at the particular time determined by Step 730. In another example, the unsuitable phase of the ongoing surgical procedure may differ from the determined phase of the ongoing surgical procedure at the particular time determined by Step 730. In some examples, Step 740 may access a data structure associating surgical instruments and actions to determine the likelihood that the prospective action involving the surgical instrument is about to take place based on the presence of the surgical instrument in the surgical cavity. Further, Step 740 may access a data structure associating actions and surgical phases to determine that the prospective action involving the surgical instrument is unsuitable to the phase of the ongoing surgical procedure at the particular time. In some examples, a machine learning model may be trained using training examples to determine likelihoods that prospective actions involving surgical instruments are about to take place at unsuitable phases of surgical procedures based on the presence of the surgical instruments in surgical cavities at particular times and the phases of the surgical procedures at the particular times. An example of such training example may include an indication of a presence of a sample surgical instrument in a sample surgical cavity at a specific time, and an indication of a phase of a sample surgical procedure at the specific time, together with a label indicating the likelihood that a sample prospective action involving the sample surgical instrument is about to take place at unsuitable phase of the sample surgical procedure. Step 740 may use the trained machine learning model to determine the likelihood that a prospective action involving the surgical instrument is about to take place at an unsuitable phase of the ongoing surgical procedure based on the presence of the surgical instrument in the surgical cavity at the particular time (detected by Step 720) and the phase of the ongoing surgical procedure at the particular time determined by Step 730. In one example, the machine learning model may be a regression model, and the likelihood may be an estimated probability (for example, between 0 and 1). In another example, the machine learning model may be a classification model, the classification model may classify the input to a particular class of a plurality of alternative classes, each alternative class may be associated with a likelihood or range of likelihoods (such as 'High', 'Medium', 'Low', etc.), and the likelihood may be based on the association of the particular class with a likelihood or range of likelihoods.

In some examples, surgical footage (such as the surgical footage received by Step 710) may be analyzed to determine at least one alternative prospective action (that is, alternative to the prospective action of Step 740 and Step 750). For example, a machine learning model may be trained using training examples to determine alternative prospective actions from surgical images and/or surgical videos. An example of such training example may include a sample surgical image or sample surgical video, together with a label indicating one or more alternative prospective actions corresponding to the sample surgical image or sample surgical video. The trained machine learning model may be used to analyze the surgical footage to determine the at least one alternative prospective action. In one example, a data structure associating surgical instruments with alternative prospective actions may be accessed based on the surgical instrument detected by Step 720 to determine the at least one alternative prospective action. In one example, a data structure associating combinations of surgical instruments and surgical phases with alternative prospective actions may be accessed based on the surgical instrument detected by Step 720 and the phase of the ongoing surgical procedure at the particular time determined by Step 730 to determine the at least one alternative prospective action. In one example, a data structure associating surgical phases with alternative prospective actions may be accessed based on the phase of the ongoing surgical procedure at the particular time determined by Step 730 to determine the at least one alternative prospective action. In some examples, a relationship between the at least one alternative prospective action and the surgical instrument detected by Step 720 may be determined. For example, a statistical model may be used to determine a statistical relationship between the at least one alternative prospective action and the surgical instrument detected by Step 720. In another example, a graph data structure with edges connecting nodes of prospective actions and nodes of surgical instruments may be accessed based on the on the surgical instrument detected by Step 720 and the determined at least one alternative prospective action to determine the relationship based on the existence of an edge between the two, or based on a weight or a label associated with an edge connecting the two. In some examples, Step 740 may further base the determination of the likelihood that the prospective action involving the surgical instrument is about to take place at the unsuitable phase of the ongoing surgical procedure on the relationship between the at least one alternative prospective action and the surgical instrument detected by Step 720. For example, when an alternative prospective action is determined, and the alternative prospective action is closely related to the surgical instrument, Step 740 may determine a higher likelihood, and when no alternative prospective action is determined or the determined alternative prospective action is only loosely related to the surgical instrument, Step 740 may determine a lower likelihood.

In some examples, surgical footage (such as the surgical footage received by Step 710) may be analyzed to identify a time sensitive situation, for example using Step 920 described below. In some examples, a relationship between the time sensitive situation and the surgical instrument detected by Step 720 may be determined. For example, a statistical model may be used to determine a statistical relationship between the time sensitive situation and the surgical instrument detected by Step 720. In another example, a graph data structure with edges connecting nodes of time sensitive situations and nodes of surgical instruments may be accessed based on the on the surgical instrument detected by Step 720 and the determined time sensitive situation to determine the relationship based on the existence of an edge between the two, or based on a weight or a label associated with an edge connecting the two. In yet another example, the surgical footage may be analyzed to determine the relationship between the time sensitive situation and the surgical instrument. For example, a visual classification model may be used to analyze the surgical footage, an indication of the time sensitive situation and an indication of the surgical instrument to classify the relationship between the time sensitive situation and the surgical instrument to a relation class (such as 'Not Related', 'Related', 'Closely Related', 'Loosely Related', and so forth). In another example, a regression model may be used to analyze the surgical footage received by Step 710, an indication of the time sensitive situation and an indication of the surgical instrument to determine a degree of the relationship between the time sensitive situation and the surgical instrument. In some examples, Step 740 may further base the determination of the likelihood that the prospective action involving the surgical instrument is about to take place at the unsuitable phase of the ongoing surgical procedure on the relationship between the time sensitive situation and the surgical instrument detected by Step 720. For example, when a time sensitive situation is determined, and the time sensitive situation is closely related to the surgical instrument. Step 740 may determine a higher likelihood, and when no time sensitive situation is determined or the determined time sensitive situation is only loosely related to the surgical instrument, Step 740 may determine a lower likelihood.

In some examples, surgical footage (such as the surgical footage received by Step 710) may be analyzed to attempt to identify a visual indicator of an intention to use the surgical instrument detected by Step 720 to perform the prospective action of Step 740 and Step 750. For example, a machine learning model may be trained using training examples to determine intentions to perform prospective actions from images and/or videos. An example of such training example may include a sample image or sample video of a sample surgical instrument in a surgical cavity, together with a label indicating whether there is an intention to perform a sample prospective action. The trained machine learning model may be used to analyze the surgical footage to attempt to identify the visual indicator of the intention to use the surgical instrument detected by Step 720 to perform the prospective action of Step 740 and Step 750. In another example, the visual indicator of the intention to use the surgical instrument detected by Step 720 to perform the prospective action of Step 740 and Step 750 may include at least one of a configuration of the surgical instrument, position of at least part of the surgical instrument or movement of at least part of the surgical instrument, and the surgical footage received by Step 710 may be analyzed to attempt to identify the visual indicator. In some examples, Step 740 may further base the determination of the likelihood that the prospective action involving the surgical instrument is about to take place at the unsuitable phase of the ongoing surgical procedure on whether the attempt to identify the visual indicator is successful. For example, when the visual indicator of the intention to use the surgical instrument detected by Step 720 to perform the prospective action of Step 740 and Step 750 is identified. Step 740 may determine a higher likelihood, and when no visual indicator of an intention to use the surgical instrument detected by Step 720 to perform the prospective action of Step 740 and Step 750 is identified, Step 740 may determine a lower likelihood.

In some examples, surgical footage (such as the surgical footage received by Step 710) may be analyzed to detect a movement of at least part of the surgical instrument, for example using a visual motion detection algorithm. In one example, the movement of the at least part of the surgical instrument may be a movement relative to an anatomical structure. In one example, the movement of the at least part of the surgical instrument may be a movement relative to at least one other part of the surgical instrument. In some examples, Step 740 may further base the determination of the likelihood that the prospective action involving the surgical instrument is about to take place at the unsuitable phase of the ongoing surgical procedure on the detected movement of the at least part of the surgical instrument. For example, when a movement of the at least part of the surgical instrument is detected, Step 740 may determine a higher likelihood, and when no movement of the at least part of the surgical instrument is detected. Step 740 may determine a lower likelihood. In another example, when the detected movement of the at least part of the surgical instrument is of one magnitude, Step 740 may determine a higher likelihood, and when the detected movement of the at least part of the surgical instrument is of another magnitude, Step 740 may determine a lower likelihood. In yet another example, when the detected movement of the at least part of the surgical instrument is in one direction, Step 740 may determine a higher likelihood, and when the detected movement of the at least part of the surgical instrument is in another direction, Step 740 may determine a lower likelihood.

In some examples, surgical footage (such as the surgical footage received by Step 710) may be analyzed to detect a position of at least part of the surgical instrument in the surgical cavity, for example using a visual object detection algorithm. In one example, the position of the at least part of the surgical instrument in the surgical cavity may be a position relative to the at least one image sensor of Step 710, may be a position relative to an anatomical structure, may be a position relative to a second surgical instrument, and so forth. In some examples, Step 740 may further base the determination of the likelihood that the prospective action involving the surgical instrument is about to take place at the unsuitable phase of the ongoing surgical procedure on the detected position of the at least part of the surgical instrument in the surgical cavity. For example, when the detected position of the at least part of the surgical instrument is at a first distance from a particular object (such as a particular anatomical structure, a second surgical instrument, etc.), Step 740 may determine a higher likelihood, and when the detected position of the at least part of the surgical instrument is at a second distance from the particular object, Step 740 may determine a lower likelihood.

In some examples, surgical footage (such as the surgical footage received by Step 710) may be analyzed to determine a configuration of at least part of the surgical instrument. Some non-limiting examples of such configuration may include 'Closed', 'Open', 'Folded', 'Unfolded', 'With Tip', 'With Extension', and so forth. For example, a machine learning model may be trained using training examples to determine configurations of surgical instruments from images and/or videos. An example of such training example may include a sample image or video of a sample surgical instrument, together with a label indicating a configuration of the sample surgical instrument. The trained machine learning model may be used to analyze the surgical footage to determine the configuration of the at least part of the surgical instrument. In some examples, Step 740 may further base the determination of the likelihood that the prospective action involving the surgical instrument is about to take place at the unsuitable phase of the ongoing surgical procedure on the configuration of the at least part of the surgical instrument. For example, when the configuration of the at least part of the surgical instrument is a first configuration (such as 'With Tip', 'Open' or 'Unfolded'). Step 740 may determine a higher likelihood, and when the configuration of the at least part of the surgical instrument is a second configuration (such as 'Without Tip', 'Closed' or 'Folded'), Step 740 may determine a lower likelihood.

In some examples, an indication of a surgical approach associated with the ongoing surgical procedure may be received. For example, receiving the indication may include reading the indication from memory. In another example, receiving the indication may include receiving the indication from an external device, for example using a digital communication device. In yet another example, receiving the indication may include determining the indication. For example, surgical footage (such as the surgical footage received by Step 710) may be analyzed to determine the surgical approach associated with the ongoing surgical procedure. For example, the surgical footage may be analyzed using a visual classification model to one or a plurality of alternative classes, each alternative class may correspond to a surgical approach, and thereby the classification determines the surgical approach associated with the ongoing surgical procedure. In some examples, Step 740 may further base the determination of the likelihood that the prospective action involving the surgical instrument is about to take place at the unsuitable phase of the ongoing surgical procedure on the surgical approach associated with the ongoing surgical procedure. For example, when the surgical approach associated with the ongoing surgical procedure is one surgical approach, Step 740 may determine one likelihood, and when the surgical approach associated with the ongoing surgical procedure is another surgical approach, Step 740 may determine another likelihood.

In some examples, patient information associated with the ongoing surgical procedure may be received. For example, receiving the patient information may include reading the patient information from memory. In another example, receiving the patient information may include receiving the patient information from an external device, for example using a digital communication device. In yet another example, receiving the patient information may include determining the patient information. For example, the surgical footage may be analyzed using a visual classification model to one or a plurality of alternative classes, each alternative class may correspond to one or more patient characteristics, and thereby the classification determines the patient information associated with the ongoing surgical procedure. In some examples, Step 740 may further base the determination of the likelihood that the prospective action involving the surgical instrument is about to take place at the unsuitable phase of the ongoing surgical procedure on the patient information. For example, when the patient information associated with the ongoing surgical procedure indicates one patient characteristic, Step 740 may determine one likelihood, and when the patient information associated with the ongoing surgical procedure indicates another patient characteristic, Step 740 may determine another likelihood.

In some examples, Step 750 may comprise, based on the likelihood determined by Step 740, providing a digital signal before the prospective action of Step 740 takes place. For example, Step 750 may provide the digital signal to a memory unit to cause the memory unit to store selected information. In another example, Step 750 may provide the digital signal to an external device, for example by transmitting the digital signal using a digital communication device over a digital communication line or digital communication network. In one example, when the likelihood determined by Step 740 is above a selected threshold, Step 750 may provide the digital signal, and when the likelihood determined by Step 740 is below the selected threshold, Step 750 may avoid providing the digital signal. In another example, when the likelihood determined by Step 740 is above a selected threshold, Step 750 may provide a first digital signal, and when the likelihood determined by Step 740 is below the selected threshold. Step 750 may provide a second digital signal, the second digital signal may differ from the first digital signal.

In some examples, the digital signal provided by Step 750 may be indicative of the prospective action. For example, the digital signal provided by Step 750 may include a digital code associated with a type of the prospective action. In some examples, the digital signal provided by Step 750 may be indicative of the determined likelihood that the prospective action involving the surgical instrument is about to take place at an unsuitable phase of the ongoing surgical procedure. For example, the digital signal provided by Step 750 may include a digital encoding of the likelihood. In some examples, the digital signal provided by Step 750 may be indicative of the phase of the ongoing surgical procedure at the particular time, and/or of the unsuitable phase of the ongoing surgical procedure. For example, the digital signal provided by Step 750 may include a digital code associated with the phase and/or a digital code associated with the unsuitable phase. In some examples, the digital signal provided by Step 750 may be indicative of the surgical instrument. For example, the digital signal provided by Step 750 may include a digital code associated with a type of the surgical instrument. In some examples, the digital signal provided by Step 750 may be indicative of the surgical cavity. For example, the digital signal provided by Step 750 may include a digital encoding of at least one of a size of the surgical cavity, type of the surgical cavity or location of the surgical cavity.

In some examples, the digital signal provided by Step 750 may be indicative of an additional action recommended for execution before the prospective action. For example, the digital signal provided by Step 750 may include a digital code associated with a type of the additional action recommended for execution before the prospective action. In one example, the additional action recommended for execution before the prospective action may be determined, for example based on the phase of the ongoing surgical procedure at the particular time determined by Step 730 and/or the surgical instrument detected by Step 720.

In some examples, Step 750 may comprise providing the digital signal to a device. For example, Step 750 may use a digital communication apparatus to transmit the digital signal to the device. In another example, Step 750 may store the digital signal in a memory shared with the device. In some examples, the digital signal provided by Step 750 to the device may be configured to cause the device to withhold the surgical instrument from performing the prospective action. For example, the device may be a robot controlling the surgical instrument, and the digital signal provided by Step 750 may be configured to cause the robot to refrain from the prospective action. In another example, the device may be an override device able to override commands to the surgical instrument, and the digital signal provided by Step 750 may be configured to cause the override device to override commands associated with the prospective action.

In some examples, Step 750 may comprise providing the digital signal to a device, for example as described above. In some examples, the digital signal provided by Step 750 to the device may be configured to cause the device to provide information to a surgeon controlling the surgical instrument. For example, the device may include an audio speaker, and the information may be provided to the surgeon audibly. In another example, the device may include a visual presentation apparatus (such as a display screen, a projector, a head mounted display, an extended reality display system, etc.), and the information may be provided to the surgeon visually, graphically or textually. In one example, the information provided to the surgeon may include at least one of an indication of an anatomical structure, indication of the prospective action, an indication of an additional action recommended for execution before the prospective action, an indication of the likelihood that the prospective action involving the surgical instrument is about to take place at the unsuitable phase of the ongoing surgical procedure, an indication of the unsuitable phase of the ongoing surgical procedure, an indication of the phase of the ongoing surgical procedure at the particular time, an indication of the surgical instrument or an indication of the surgical cavity. In one example, the information provided to the surgeon may include at least part of the surgical footage received by Step 710. In some examples, a portion of the surgical footage captured after the digital signal is provided may be analyzed to identify a particular action taking place in the ongoing surgical procedure, for example using a visual action recognition algorithm. The particular action may differ from the prospective action. Further, based on the identified particular action, a second digital signal may be provided to the device before the prospective action takes place. The second digital signal may be configured to cause the device to modify the information provided to the surgeon. For example, the information may be visually presented (for example, on a display screen, using a projector, using a head mounted display, using an extended reality display system, etc.), and modifying the information may include modifying the visual presentation to present a modified version of the information.

In some examples, surgical footage (such as the surgical footage received by Step 710) may be analyzed to determine that an anatomical structure is inaccessible for a safe performance of the prospective action of Step 740. For example, a machine learning model may be trained using training examples to determine that anatomical structures are inaccessible for safe performances of prospective actions from images and/or videos. An example of such training example may include a sample image or a sample video of a sample anatomical structure and an indication of a sample prospective action, together with a label indicating whether the sample anatomical structure is inaccessible for a safe performance of the sample prospective action. The trained machine learning model may be used to analyze at least part of the surgical footage to determine whether the anatomical structure is inaccessible for a safe performance of the prospective action of Step 740. In another example, at least part of the surgical footage may be analyzed using an object detection algorithm to detect and determine the locations of the anatomical structure and nearby structures, and the determination of whether the anatomical structure is inaccessible for a safe performance of the prospective action of Step 740 may be based on the determined locations. In yet another example, at least part of the surgical footage may be analyzed using an object detection algorithm to determine whether a particular part of the anatomical structure is visible, and the determination of whether the anatomical structure is inaccessible for a safe performance of the prospective action of Step 740 may be based on whether the particular part of the anatomical structure is visible. In some examples, Step 740 may further base the determination of the likelihood that the prospective action involving the surgical instrument is about to take place at the unsuitable phase of the ongoing surgical procedure on the determination that the anatomical structure is inaccessible for the safe performance of the prospective action. For example, when the anatomical structure is inaccessible for the safe performance of the prospective action at the particular time, Step 740 may determine a higher likelihood, and when the anatomical structure is accessible for the safe performance of the prospective action at the particular time, Step 740 may determine a lower likelihood. In some examples, the digital signal provided by Step 750 may be indicative of the anatomical structure. For example, the digital signal may include a digital code associated with the anatomical structure.

Typically, a surgery is a focused endeavor to achieve a desired predetermined goals.

However, during surgery, opportunities to perform other unplanned actions that may benefit the patient may arise. For example, an opportunity to treat a previously unknown condition that was discovered during the surgery may arise. In another example, an opportunity to diagnose a previously unsuspected condition may arise, for example through biopsy. Unfortunately, in many cases the surgeon conducting the surgery are focused on the desired predetermined goals, and may miss the opportunities to perform other unplanned actions that may benefit the patient. It is therefore beneficial to automatically identify the opportunities to perform other unplanned actions that may benefit the patient, and to notify the surgeons about the identified opportunities.

Systems, methods, and non-transitory computer readable media for triggering removal of tissue for biopsy in an ongoing surgical procedure are provided. For example, a system for triggering removal of tissue for biopsy in an ongoing surgical procedure may include at least one processor, as described above, and the processor may be configured to perform the steps of process 800. In another example, a computer readable medium for triggering removal of tissue for biopsy in an ongoing surgical procedure, such as a non-transitory computer readable medium, may store data and/or computer implementable instructions that, when executed by at least one processor, causes the at least one processor to perform operations for carrying out the steps of process 800. In other examples, the steps of process 800 may be carried out by any means.

Figure 8:
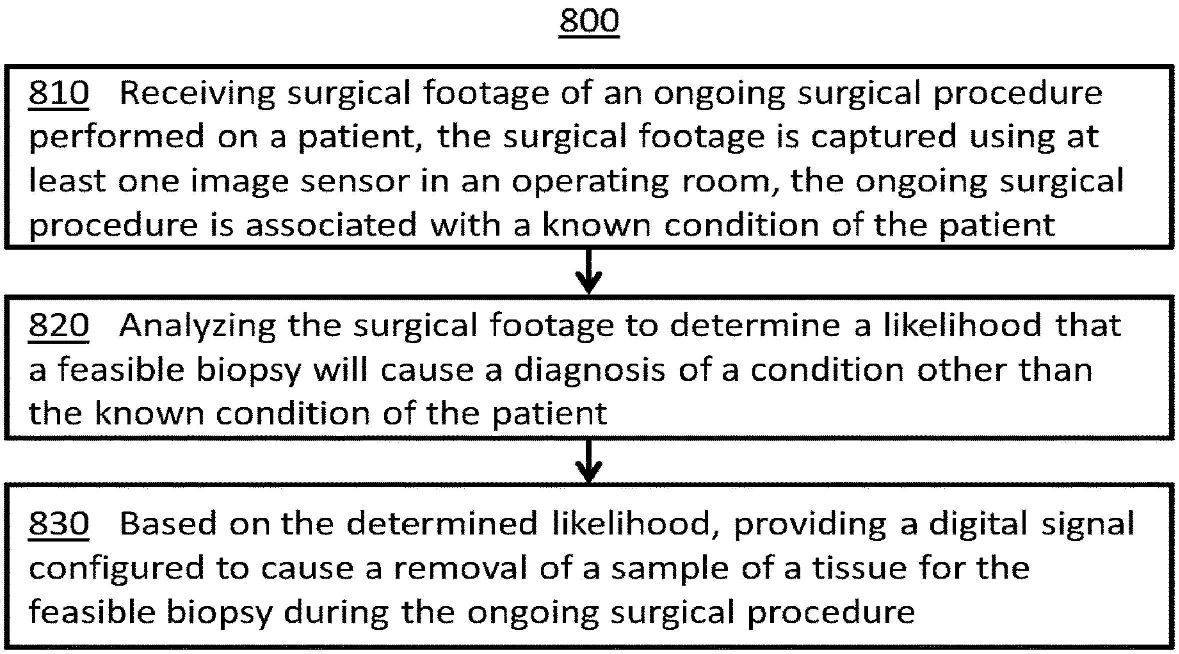
FIG. 8 is a flowchart illustrating an exemplary process for triggering removal of tissue for biopsy in an ongoing surgical procedure, consistent with disclosed embodiments.

FIG. 8 is a flowchart illustrating an exemplary process 800 for triggering removal of tissue for biopsy in an ongoing surgical procedure, consistent with disclosed embodiments. In this example, process 800 may comprise: receiving surgical footage of an ongoing surgical procedure performed on a patient (Step 810), the surgical footage may be a surgical footage captured using at least one image sensor in an operating room, and the ongoing surgical procedure may be associated with a known condition of the patient; analyzing the surgical footage to determine a likelihood that a feasible biopsy will cause a diagnosis of a condition other than the known condition of the patient (Step 820); and, based on the determined likelihood, providing a digital signal configured to cause a removal of a sample of a tissue for the feasible biopsy during the ongoing surgical procedure (Step 830).

In some examples, Step 810 may comprise receiving surgical footage of an ongoing surgical procedure performed on a patient. The surgical footage may be a surgical footage captured using at least one image sensor in an operating room. The ongoing surgical procedure may be associated with a known condition of the patient. In one example, the received surgical footage of the ongoing surgical procedure may include surgical footage captured using at least one of overhead camera 115, overhead camera 121, overhead camera 123, tableside camera 125 or image sensors 421. In some examples, receiving surgical footage by Step 810 may include reading the surgical footage from memory. In some examples, receiving surgical footage by Step 810 may include receiving the surgical footage from an external device, for example using a digital communication device via a digital communication line or a digital communication network. In some examples, receiving surgical footage by Step 810 may include capturing the surgical footage using the at least one image sensor.

In some examples, Step 820 may comprise analyzing surgical footage (such as the surgical footage received by Step 810) to determine a likelihood that a feasible biopsy will cause a diagnosis of a condition other than the known condition of the patient. For example, a machine learning model may be trained using training examples to determine likelihoods that feasible biopsies will cause diagnosis of different conditions from images and/or videos. An example of such training example may include a sample image or video of a sample surgical procedure, together with a label indicating the likelihood that a feasible biopsy in the sample surgical procedure will cause a particular diagnosis. Step 820 may use the trained machine learning model to analyze the surgical footage to determine a likelihood that a feasible biopsy will cause a diagnosis of a condition other than the known condition of the patient. In another example, Step 820 may analyze at least part of the surgical footage received by Step 810 to calculate a convolution of the at least part of the surgical footage received by Step 810 and thereby obtain a result value of the calculated convolution. Further, in response to the result value of the calculated convolution being a first value, Step 820 may determine that the likelihood that the feasible biopsy will cause the diagnosis of the condition other than the known condition of the patient is one likelihood (for example, 'High'. '80%', and so forth), and in response to the result value of the calculated convolution being a second value, Step 820 may determine that the likelihood that the feasible biopsy will cause the diagnosis of the condition other than the known condition of the patient is another likelihood (for example, Low. '30%', and so forth). In some examples, an indication of a plurality of known conditions of the patient may be received, for example from a memory unit, from an external device, from a medical record, from an Electronic Medical Records (EMR) system, from a user (for example, through a user interface), and so forth. Further, the condition other than the known condition of the patient may be a condition not included in the plurality of known conditions of the patient. In one example, the plurality of known conditions of the patient may include at least one condition of the patient not associated with the ongoing surgical procedure.

In some examples, the condition other than the known condition of the patient may be endometriosis. Further, the surgical footage received by Step 810 may be analyzed to attempt to identify a visual indication of endometriosis, and Step 820 may base the determination of the likelihood that the feasible biopsy will cause the diagnosis of endometriosis on whether the attempt is successful. For example, the visual indication of endometriosis may include a lesion. Endometriosis lesions are typically can appear dark blue, powder-burn black, red, white, yellow, brown or non-pigmented, and can vary in size, commonly appearing on the ovaries, fallopian tubes, outside surface of the uterus or ligaments surrounding the uterus, but may also appear on the vulva, vagina, cervix, bladder, ureters, intestines or rectum. When a lesion matching these criteria appear in the surgical footage received by Step 810, a visual indication of endometriosis may be successfully identify, and Step 820 may determine a high likelihood that the feasible biopsy will cause the diagnosis of endometriosis. In another example, a machine learning model may be trained using training examples to identify visual indications of endometriosis in images and/or videos. An example of such training example may include a sample image or video, together with a label indicating whether the sample image or video includes a visual indication of endometriosis. The trained machine learning model may be used to analyze the surgical footage and attempt to identify a visual indication of endometriosis. In one example, when the attempt to identify the visual indication of endometriosis is successful, Step 820 may determine a high likelihood that the feasible biopsy will cause the diagnosis of endometriosis, and when the attempt to identify the visual indication of endometriosis is unsuccessful, Step 820 may determine a low likelihood that the feasible biopsy will cause the diagnosis of endometriosis.

In some examples, the surgical footage received by Step 810 may be analyzed to determine a shape of at least part of an anatomical structure of the patient, and Step 820 may base the determination of the likelihood that the feasible biopsy will cause the diagnosis of the condition other than the known condition of the patient on the shape of the at least part of the anatomical structure of the patient. For example, the surgical footage may be analyzed using a semantic segmentation algorithm to determine the shape of the at least part of the anatomical structure of the patient. In another example, the surgical footage may be analyzed using a template matching algorithm to determine the shape of the at least part of the anatomical structure of the patient. In some examples, an anatomical structure may have a typical shape, and deviation from this typical shape may indicate a plausibility of a medical condition. The surgical footage may be analyzed to identify a deviation of the shape of the anatomical structure from the typical shape. When the shape of the anatomical structure deviates from the typical shape, Step 820 may determine a high likelihood that the feasible biopsy will cause the diagnosis of the condition other than the known condition of the patient, and when the shape of the anatomical structure does not deviate from the typical shape, Step 820 may determine a low likelihood that the feasible biopsy will cause the diagnosis of the condition other than the known condition of the patient. In some examples, an anatomical structure may normally have a symmetric shape, and deviation from this symmetry may indicate a plausibility of a medical condition. The surgical footage may be analyzed to determine whether the shape of the anatomical structure is symmetrical. When the shape of the anatomical structure is asymmetric. Step 820 may determine a high likelihood that the feasible biopsy will cause the diagnosis of the condition other than the known condition of the patient, and when the shape of the anatomical structure is symmetric. Step 820 may determine a low likelihood that the feasible biopsy will cause the diagnosis of the condition other than the known condition of the patient. In some examples, a lesion associated with the condition other than the known condition of the patient may have a typical shape. The surgical footage may be analyzed to detect anatomical structures of this typical lesion shape. When an anatomical structure of this typical lesion shape is detected. Step 820 may determine a high likelihood that the feasible biopsy will cause the diagnosis of the condition other than the known condition of the patient, and when no anatomical structure of this typical lesion shape is detected. Step 820 may determine a low likelihood that the feasible biopsy will cause the diagnosis of the condition other than the known condition of the patient. In some examples, when the shape of the at least part of the anatomical structure of the patient is a first shape. Step 820 may determine a high likelihood that the feasible biopsy will cause the diagnosis of the condition other than the known condition of the patient, and when the shape of the at least part of the anatomical structure of the patient is a second shape. Step 820 may determine a low likelihood that the feasible biopsy will cause the diagnosis of the condition other than the known condition of the patient. In one example, the first and second shapes may be selected based on the condition other than the known condition of the patient.

In some examples, the surgical footage may be analyzed to determine a color of at least part of an anatomical structure of the patient, and Step 820 may base the determination of the likelihood that the feasible biopsy will cause the diagnosis of the condition other than the known condition of the patient on the color of the at least part of the anatomical structure of the patient. For example, pixel data of the surgical footage may be sampled to determine the color of the at least part of the anatomical structure of the patient. In some examples, an anatomical structure may have a typical color, and deviation from this typical color may indicate a plausibility of a medical condition. The surgical footage may be analyzed to identify a deviation of the color of the anatomical structure from the typical color. When the color of the anatomical structure deviates from the typical color. Step 820 may determine a high likelihood that the feasible biopsy will cause the diagnosis of the condition other than the known condition of the patient, and when the color of the anatomical structure does not deviate from the typical color. Step 820 may determine a low likelihood that the feasible biopsy will cause the diagnosis of the condition other than the known condition of the patient. In some examples, a lesion associated with the condition other than the known condition of the patient may have a typical color. The surgical footage may be analyzed to detect anatomical structures of this typical lesion color. When an anatomical structure of this typical lesion color is detected. Step 820 may determine a high likelihood that the feasible biopsy will cause the diagnosis of the condition other than the known condition of the patient, and when no anatomical structure of this typical lesion color is detected, Step 820 may determine a low likelihood that the feasible biopsy will cause the diagnosis of the condition other than the known condition of the patient. In some examples, when the color of the at least part of the anatomical structure of the patient is a first color, Step 820 may determine a high likelihood that the feasible biopsy will cause the diagnosis of the condition other than the known condition of the patient, and when the color of the at least part of the anatomical structure of the patient is a second color, Step 820 may determine a low likelihood that the feasible biopsy will cause the diagnosis of the condition other than the known condition of the patient. In one example, the first and second colors may be selected based on the condition other than the known condition of the patient.

In some examples, the surgical footage may be analyzed to determine a texture of at least part of an anatomical structure of the patient, and Step 820 may base the determination of the likelihood that the feasible biopsy will cause the diagnosis of the condition other than the known condition of the patient on the texture of the at least part of the anatomical structure of the patient. For example, pixel data of the surgical footage may be analyzed using a filter to determine the texture of the at least part of the anatomical structure of the patient. In some examples, an anatomical structure may have a typical texture, and deviation from this typical texture may indicate a plausibility of a medical condition. The surgical footage may be analyzed to identify a deviation of the texture of the anatomical structure from the typical texture. When the texture of the anatomical structure deviates from the typical texture, Step 820 may determine a high likelihood that the feasible biopsy will cause the diagnosis of the condition other than the known condition of the patient, and when the texture of the anatomical structure does not deviate from the typical texture, Step 820 may determine a low likelihood that the feasible biopsy will cause the diagnosis of the condition other than the known condition of the patient. In some examples, a lesion associated with the condition other than the known condition of the patient may have a typical texture. The surgical footage may be analyzed to detect anatomical structures of this typical lesion texture. When an anatomical structure of this typical lesion texture is detected, Step 820 may determine a high likelihood that the feasible biopsy will cause the diagnosis of the condition other than the known condition of the patient, and when no anatomical structure of this typical lesion texture is detected, Step 820 may determine a low likelihood that the feasible biopsy will cause the diagnosis of the condition other than the known condition of the patient. In some examples, when the texture of the at least part of the anatomical structure of the patient is a first texture, Step 820 may determine a high likelihood that the feasible biopsy will cause the diagnosis of the condition other than the known condition of the patient, and when the texture of the at least part of the anatomical structure of the patient is a second texture, Step 820 may determine a low likelihood that the feasible biopsy will cause the diagnosis of the condition other than the known condition of the patient. In one example, the first and second textures may be selected based on the condition other than the known condition of the patient.

In some examples, the surgical footage may be analyzed to determine a size of at least part of an anatomical structure of the patient, and Step 820 may base the determination of the likelihood that the feasible biopsy will cause the diagnosis of the condition other than the known condition of the patient on the size of the at least part of the anatomical structure of the patient. For example, the surgical footage may be analyzed using a semantic segmentation algorithm to determine the size of the at least part of the anatomical structure of the patient. In another example, the surgical footage may include a range image, and the range image may be analyzed to determine the size of the at least part of the anatomical structure of the patient. In some examples, an anatomical structure may have a typical size, and deviation from this typical size may indicate a plausibility of a medical condition. The surgical footage may be analyzed to identify a deviation of the size of the anatomical structure from the typical size. When the size of the anatomical structure deviates from the typical size. Step 820 may determine a high likelihood that the feasible biopsy will cause the diagnosis of the condition other than the known condition of the patient, and when the size of the anatomical structure does not deviate from the typical size. Step 820 may determine a low likelihood that the feasible biopsy will cause the diagnosis of the condition other than the known condition of the patient. In some examples, a lesion associated with the condition other than the known condition of the patient may have a typical size. The surgical footage may be analyzed to detect anatomical structures of this typical lesion size. When an anatomical structure of this typical lesion size is detected. Step 820 may determine a high likelihood that the feasible biopsy will cause the diagnosis of the condition other than the known condition of the patient, and when no anatomical structure of this typical lesion size is detected. Step 820 may determine a low likelihood that the feasible biopsy will cause the diagnosis of the condition other than the known condition of the patient. In some examples, when the size of the at least part of the anatomical structure of the patient is a first size. Step 820 may determine a high likelihood that the feasible biopsy will cause the diagnosis of the condition other than the known condition of the patient, and when the size of the at least part of the anatomical structure of the patient is a second size. Step 820 may determine a low likelihood that the feasible biopsy will cause the diagnosis of the condition other than the known condition of the patient. In one example, the first and second size s may be selected based on the condition other than the known condition of the patient.

In some examples, background medical information associated with a patient (such as the patient of process 800) may be received. For example, receiving the background medical information may comprise reading the background medical information from memory. In another example, the background medical information may be received from an external device (for example, using a digital communication device), may be received from a medical record, may be received from an EMR system, from a user (for example, through a user interface), and so forth. In some examples. Step 820 may base the determination of the likelihood that the feasible biopsy will cause the diagnosis of the condition other than the known condition of the patient on an analysis of the background medical information associated with the patient. For example, the background medical information may indicate that the patient has a risk factor associated with the condition other than the known condition of the patient, and in response to the risk factor Step 820 may determine a higher likelihood that the feasible biopsy will cause the diagnosis of the condition other than the known condition of the patient. For example, the risk factor may include at least one of gender, age, obesity, another medical condition, or history of the condition other than the known condition of the patient in the family of the patient. In some examples, a machine learning model may be trained using training examples to determine likelihoods that feasible biopsies will cause diagnosis of different conditions based on background medical information. An example of such training example may include a sample background medical information, together with a label indicating the likelihood that a feasible biopsy in the sample surgical procedure will cause a particular diagnosis. Step 820 may use the trained machine learning model to analyze the received background medical information to determine a likelihood that a feasible biopsy will cause a diagnosis of a condition other than the known condition of the patient.

In some examples, Step 830 may comprise, based on a likelihood that a feasible biopsy will cause a diagnosis of a condition other than the known condition of the patient (such as the likelihood determined by Step 820), providing a digital signal configured to cause a removal of a sample of a tissue for the feasible biopsy during the ongoing surgical procedure. For example, Step 830 may provide the digital signal to a memory unit to cause the memory unit to store selected information. In another example, Step 830 may provide the digital signal to an external device, for example by transmitting the digital signal using a digital communication device over a digital communication line or digital communication network. In one example, when the likelihood is greater than a selected threshold, Step 830 may provide the digital signal, and when the likelihood is lower than the selected threshold, Step 830 may avoid providing the digital signal. In one example, when the likelihood is a first likelihood, Step 830 may provide a first digital signal, and when the likelihood is a second likelihood, Step 830 may provide a second digital signal. In some examples, the digital signal provided by Step 830 may be indicative of the condition other than the known condition of the patient. In some examples, the digital signal provided by Step 830 may be indicative of at least one of the likelihood determined by Step 820, the feasible biopsy, a recommended location for the removal of the sample of the tissue, a recommended surgical instrument for the removal of the sample of the tissue, or an anatomical structure associated with the tissue.

In some examples, Step 830 may provide the digital signal to a device. For example, Step 830 may use a digital communication apparatus to transmit the digital signal to the device. In another example, Step 830 may store the digital signal in a memory shared with the device. In some examples, the digital signal provided by Step 830 to the device may be configured to cause the device to provide information to a person associated with the ongoing surgical procedure. For example, the device may include an audio speaker, and the information may be provided to the person audibly. In another example, the device may include a visual presentation apparatus (such as a display screen, a projector, a head mounted display, an extended reality display system, etc.), and the information may be provided to the person visually, graphically or textually. In one example, the information provided to the person by the device may include at least part of the surgical footage. In another example, the information provided to the person by the device may include at least one of an indication of the condition other than the known condition of the patient, an indication of the likelihood determined by Step 820, an indication of the feasible biopsy, an indication of a recommended location for the removal of the sample of the tissue, an indication of a recommended surgical instrument for the removal of the sample of the tissue, or an indication of an anatomical structure associated with the tissue.

In some examples, Step 830 may comprise providing the digital signal to a medical robot, for example as described above. For example, Step 830 may use a digital communication apparatus to transmit the digital signal to the medical robot. In another example, Step 830 may store the digital signal in a memory shared with the medical robot. In some examples, the digital signal provided by Step 830 to the medical robot may be configured to cause the medical robot to remove the sample of the tissue. For example, the digital signal may encode at least one of an indication of a recommended location for the removal of the sample of the tissue, an indication of a recommended surgical instrument for the removal of the sample of the tissue, or an indication of an anatomical structure associated with the tissue.

In some examples, the surgical footage received by Step 810 may be analyzed to identify a recommended location for the removal of the sample of the tissue, and the digital signal provided by Step 830 may be indicative of the recommended location. For example, the digital signal provided by Step 830 may include a name associated with the recommended location, may include a textual description of the recommended location, may include an image of the recommended location (for example, with an overlay visually indicating of the recommended location on the image), may include an location in the surgical footage received by Step 810 associated with the recommended location, and so forth. In one example, a machine learning model may be trained using training examples to identify recommended locations for biopsies from images and/or videos. An example of such training example may include a sample image or video of a sample anatomical structure, together with a label indicating a recommended location for a removal of a sample of a tissue for biopsy from the sample anatomical structure. The trained machine learning model may be used to analyze the surgical footage received by Step 810 and identify the recommended location for the removal of the sample of the tissue.

In some examples, the surgical footage received by Step 810 may be analyzed to determine a recommended surgical instrument for the removal of the sample of the tissue, and the digital signal provided by Step 830 may be indicative of the recommended surgical instrument. For example, the digital signal provided by Step 830 may include a name of the recommended surgical instrument, may include a code associated with the recommended surgical instrument, may include an image of the recommended surgical instrument, and so forth. In one example, a machine learning model may be trained using training examples to identify recommended surgical instruments for biopsies from images and/or videos. An example of such training example may include a sample image or video of a sample anatomical structure, together with a label indicating a recommended surgical instrument for a removal of a sample of a tissue for biopsy from the sample anatomical structure. The trained machine learning model may be used to analyze the surgical footage received by Step 810 and identify the recommended surgical instrument for the removal of the sample of the tissue.

In some examples, the surgical footage may be analyzed to determine a potential risk due to a removal of a sample of the tissue for a biopsy (for example, due to the removal of the sample of the tissue for the biopsy during the ongoing surgical procedure). For example, a machine learning model may be trained using training examples to determine potential risks due to removal of samples of the tissues from images and/or videos. An example of such training example may include a sample image or video of a sample anatomical structure, together with a label indicating a risk level associated with a removal of a sample of a tissue from the sample anatomical structure for a biopsy. The trained machine learning model may be used to analyze the surgical footage and determine the potential risk due to the removal of the sample of the tissue for the biopsy during the ongoing surgical procedure. In some examples, a condition of an anatomical structure associated with the tissue may be determined. For example, a visual classification model may be used to analyze the surgical footage and classify the anatomical structure to one or a plurality of alternative classes, each class may correspond to a condition (such as 'Good', 'Poor', etc.) and thereby the condition of the anatomical structure associated with the tissue may be determined. Further, the potential risk due to the removal of the sample of the tissue for the biopsy during the ongoing surgical procedure may be determined based on the condition of the anatomical structure associated with the tissue. For example, when the condition of the anatomical structure associated with the tissue is one condition (such as 'Good'), the potential risk due to the removal of the sample of the tissue for the biopsy during the ongoing surgical procedure may be determined to be low, and when the condition of the anatomical structure associated with the tissue is another condition (such as Poor), the potential risk due to the removal of the sample of the tissue for the biopsy during the ongoing surgical procedure may be determined to be high.

In some examples, background medical information associated with the patient may be received. For example, receiving the background medical information may include reading the background medical information from memory. In another example, receiving the background medical information may include receiving the background medical information from an external device (for example, using a digital communication device), may include receiving the background medical information for a user (for example, through a user interface), may include receiving the background medical information from a medical record, may include receiving the background medical information from an EMR system, may include determining the background medical information, and so forth. In some examples, the background medical information may be analyzed to determine a potential risk due to the removal of the sample of the tissue for the biopsy during the ongoing surgical procedure. For example, a machine learning model may be trained using training examples to determine potential risks due to removal of samples of the tissues from background medical information. An example of such training example may include a sample background medical information associated with a sample patient, together with a label indicating a risk level associated with a removal of a sample of a tissue from the sample patient for a biopsy. The trained machine learning model may be used to analyze the received background medical information and determine the potential risk due to the removal of the sample of the tissue for the biopsy during the ongoing surgical procedure. In another example, when the background medical information indicates a tendency to bleed easily, the potential risk due to the removal of the sample of the tissue for the biopsy during the ongoing surgical procedure may be determined to be high, and when the background medical information does not indicate a tendency to bleed easily, the potential risk due to the removal of the sample of the tissue for the biopsy during the ongoing surgical procedure may be determined to be low.

In some examples, Step 830 may further base the providence of the digital signal configured to cause the removal of the sample of the tissue for the feasible biopsy on the potential risk due to the removal of the sample of the tissue for the biopsy during the ongoing surgical procedure (for example, on the potential risk determined by analyzing the surgical footage as described above, on the potential risk determined by analyzing the background medical information associated with the patient as described above, and so forth). For example, when the potential risk due to the removal of the sample of the tissue for the biopsy during the ongoing surgical procedure is a first risk (such as 'High'). Step 830 may avoid providing the digital signal configured to cause the removal of the sample of the tissue for the feasible biopsy, and when the potential risk due to the removal of the sample of the tissue for the biopsy during the ongoing surgical procedure is a second risk (such as 'Low'). Step 830 may provide the digital signal configured to cause the removal of the sample of the tissue for the feasible biopsy. In another example, when the potential risk due to the removal of the sample of the tissue for the biopsy during the ongoing surgical procedure is a first risk (such as 'High'). Step 830 may provide a first digital signal configured to cause the removal of the sample of the tissue for the feasible biopsy, and when the potential risk due to the removal of the sample of the tissue for the biopsy during the ongoing surgical procedure is a second risk (such as 'Low'). Step 830 may provide a second digital signal configured to cause the removal of the sample of the tissue for the feasible biopsy. For example, the first digital signal may include information configured to cause a step for reducing the potential risk, and the second digital signal may not include the information configured to cause the step for reducing the potential risk.

In some examples, a likelihood that the feasible biopsy will cause a change to an insurance eligibility of the patient may be determined. For example, current insurance eligibility of the patient may be compared with a potential insurance eligibility associated with the feasible biopsy to determine the likelihood that the feasible biopsy will cause a change to the insurance eligibility of the patient. In some examples, Step 830 may further base the providence of the digital signal configured to cause the removal of the sample of the tissue for the feasible biopsy during the ongoing surgical procedure on the likelihood that the feasible biopsy will cause the change to the insurance eligibility of the patient. For example, when the likelihood that the feasible biopsy will cause the change to the insurance eligibility of the patient is low. Step 830 may avoid providing the digital signal configured to cause the removal of the sample of the tissue for the feasible biopsy, and when the likelihood that the feasible biopsy will cause the change to the insurance eligibility of the patient is high. Step 830 may provide the digital signal configured to cause the removal of the sample of the tissue for the feasible biopsy. In another example, when the likelihood that the feasible biopsy will cause the change to the insurance eligibility of the patient is high. Step 830 may provide a first digital signal configured to cause the removal of the sample of the tissue for the feasible biopsy, and when the likelihood that the feasible biopsy will cause the change to the insurance eligibility of the patient is low. Step 830 may provide a second digital signal configured to cause the removal of the sample of the tissue for the feasible biopsy. The second digital signal may differ from the first digital signal.

In some examples, a stage of the ongoing surgical procedure for the removal of the sample of the tissue may be selected. For example, a data structure associating biopsies with preferred stages of surgical procedures may be accessed based on the feasible biopsy to select the stage of the ongoing surgical procedure for the removal of the sample of the tissue. In some examples, the surgical footage received by Step 810 may be analyzed to identify that the stage of the ongoing surgical procedure has been reached. For example, a machine learning model may be trained using training examples to identify stages of surgical procedures from images and/or videos. An example of such training examples may include a sample image or video of a portion of a sample surgical procedure, together with a label indicating a stage corresponding to the portion of the sample surgical procedure. The trained machine learning model may be used to analyze the surgical footage received by Step 810 to identify the stages of the ongoing surgical procedure, and to identify when the stage of the ongoing surgical procedure has been reached. In some examples. Step 830 may provide the digital signal after the stage of the ongoing surgical procedure has been reached.

In some examples, the surgical footage received by Step 810 may be analyzed to identify a time sensitive situation, for example as described below in relation to Step 920. In some examples. Step 830 may withhold the providence of the digital signal until the time sensitive situation is resolved. For example, a portion of the surgical footage (that is received by Step 810) captured after the time sensitive situation is identified may be analyzed to identify when the time sensitive situation is resolved, and when the time sensitive situation is resolved. Step 830 may provide the digital signal.

In some examples, a portion of the surgical footage (that is received by Step 810) captured after the digital signal is provided and before the removal of the sample of the tissue occurs may be analyzed to determine an updated likelihood that the feasible biopsy will cause the diagnosis of the condition other than the known condition of the patient. For example, the same techniques used by Step 820 (to determine the original likelihood that the feasible biopsy will cause the diagnosis of the condition other than the known condition of the patient) to analyze the portion of the surgical footage captured after the digital signal is provided and before the removal of the sample of the tissue occurs to determine the updated likelihood that the feasible biopsy will cause the diagnosis of the condition other than the known condition of the patient. Further, based on the determined updated likelihood, a second digital signal configured to prevent the removal of the sample of the tissue for the feasible biopsy during the ongoing surgical procedure may be provided. For example, the second digital signal may be provided to a memory unit to cause the memory unit to store selected information. In another example, the second digital signal may be provided to an external device, for example by transmitting the second digital signal using a digital communication device over a digital communication line or digital communication network. In yet another example, the second digital signal may be provided to a person associated with the ongoing surgical procedure, such as a surgeon.

In a surgical procedure, a surgeon may be faced with many situations that require attention simultaneously. Some of these situations may be time sensitive, where a delayed reaction may be harmful. However, notifying the surgeon about all situations that require attention, or about all time sensitive situations, may result in clutter. It is therefore desired to identify the time sensitive situations that the surgeon is likely to miss, and notify the surgeon about these situations, possibly ignoring other situations or notifying about the other situations in a different, less intensive, way.

Systems, methods, and non-transitory computer readable media for addressing time sensitive situations in surgical procedures are provided. For example, a system for addressing time sensitive situations in surgical procedures may include at least one processor, as described above, and the processor may be configured to perform the steps of process 900. In another example, a computer readable medium for addressing time sensitive situations in surgical procedures, such as a non-transitory computer readable medium, may store data and/or computer implementable instructions that, when executed by at least one processor, causes the at least one processor to perform operations for carrying out the steps of process 900. In other examples, the steps of process 900 may be carried out by any means.

Figure 9:
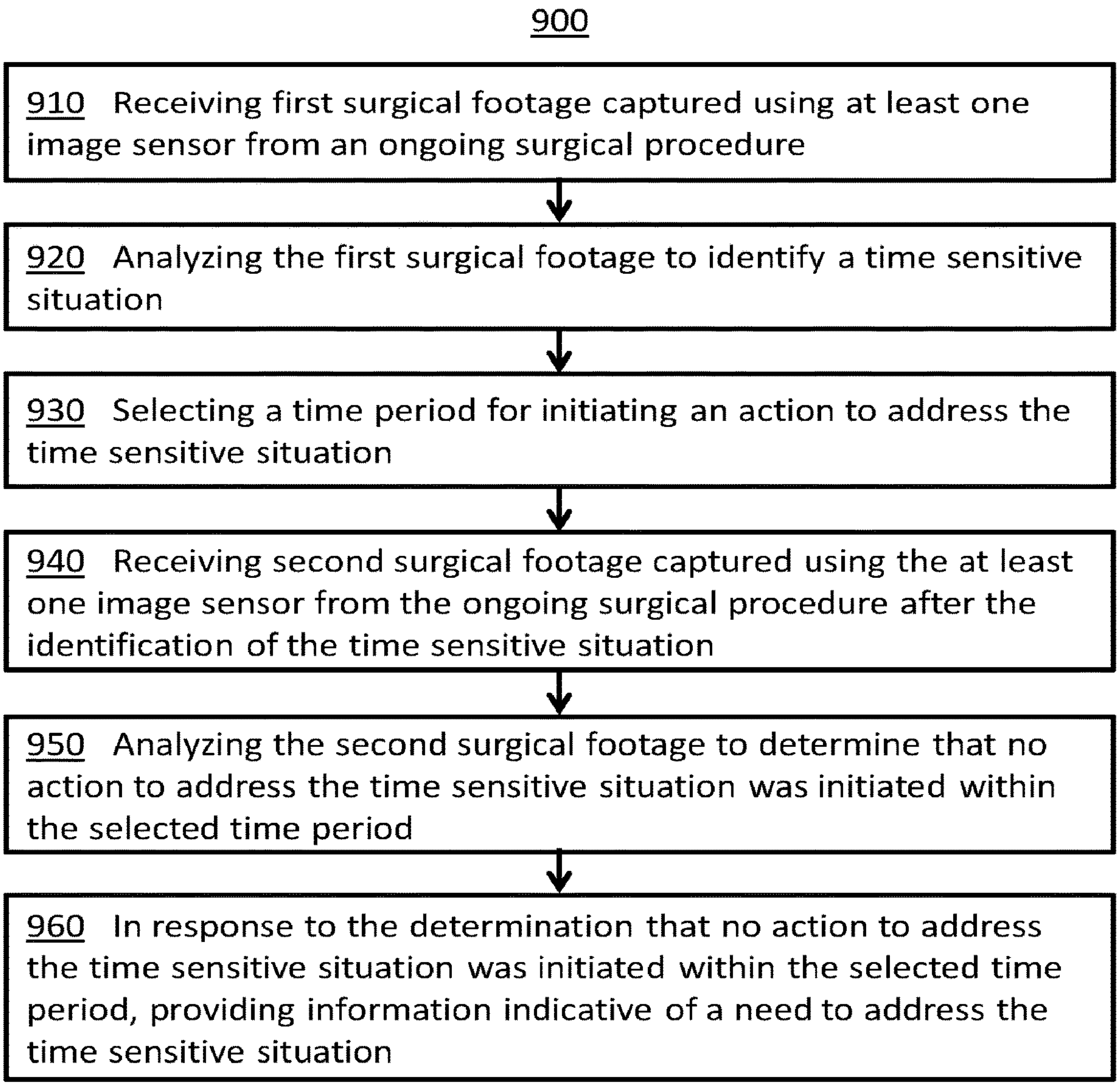
FIG. 9 is a flowchart illustrating an exemplary process for addressing time sensitive situations in surgical procedures, consistent with disclosed embodiments.

FIG. 9 is a flowchart illustrating an exemplary process 900 for addressing time sensitive situations in surgical procedures, consistent with disclosed embodiments. In this example, process 900 may comprise: receiving first surgical footage captured using at least one image sensor from an ongoing surgical procedure (Step 910); analyzing the first surgical footage to identify a time sensitive situation (Step 920); selecting a time period for initiating an action to address the time sensitive situation (Step 930); receiving second surgical footage captured using the at least one image sensor from the ongoing surgical procedure after the identification of the time sensitive situation (Step 940); analyzing the second surgical footage to determine that no action to address the time sensitive situation was initiated within the selected time period (Step 950); and, in response to the determination that no action to address the time sensitive situation was initiated within the selected time period, providing information indicative of a need to address the time sensitive situation (Step 960). In some examples, the time sensitive situation may include at least one of a bleeding, leakage, blockage of blood flow, or compression.

In some embodiments, Step 910 may comprise receiving first surgical footage captured using at least one image sensor from an ongoing surgical procedure. For example, the received first surgical footage of the ongoing surgical procedure may include surgical footage captured using at least one of overhead camera 115, overhead camera 121, overhead camera 123, tableside camera 125 or image sensors 421. In some examples, receiving the first surgical footage by Step 910 may include reading the first surgical footage from memory. In some examples, receiving the first surgical footage by Step 910 may include receiving the first surgical footage from an external device, for example using a digital communication device via a digital communication line or a digital communication network. In some examples, receiving the first surgical footage by Step 910 may include capturing the first surgical footage using the at least one image sensor.

In some examples, Step 920 may comprise analyzing surgical footage (such as the first surgical footage received by Step 910 or the surgical footage received by Step 810) to identify a time sensitive situation. For example, a machine learning model may be trained using training examples to identify time sensitive situations from images and/or videos. An example of such training example may include a surgical image or video of a sample surgical procedure, together with an indication of a time sensitive situation in the sample surgical procedure. Step 920 may use the trained machine learning model to analyze the surgical footage and identify the time sensitive situation. In some examples, Step 920 may analyze at least part of the surgical footage to calculate a convolution of the at least part of the surgical footage and thereby obtain a result value of the calculated convolution. In one example, in response to the result value of the calculated convolution being a first value, Step 920 may identify a time sensitive situation, and in response to the result value of the calculated convolution being a first value, Step 920 may avoid identifying the time sensitive situation. In another example, in response to the result value of the calculated convolution being a first value, Step 920 may identify a first time sensitive situation, and in response to the result value of the calculated convolution being a first value, Step 920 may identify a second time sensitive situation (the second time sensitive situation may differ from the first time sensitive situation). In some examples, Step 920 may provide second information in response to the identification of the time sensitive situation. The second information may differ from the information provided by Step 960 in response to the determination of Step 950 that no action to address the time sensitive situation was initiated within the selected time period. For example, Step 920 may provide the second information to a memory unit to cause the memory unit to store selected data. In another example, Step 920 may provide the second information, for example by transmitting, using a digital communication device over a digital communication line or digital communication network, a digital signal encoding the second information. In yet another example, Step 920 may provide the second information to a person, for example audibly, visually, graphically, textually, via a user interface, and so forth. In one example, the second information may be indicative of the time sensitive situation.

In some examples, Step 930 may comprise selecting a time period for initiating an action to address a time sensitive situation (such as the time sensitive situation identified by Step 920). In some examples, Step 930 may analyzing surgical footage (such as the first surgical footage received by Step 910) to select the time period for initiating the action to address the time sensitive situation. In one example, a machine learning model may be trained using training examples to select time periods for initiating actions to address time sensitive situations from images and/or videos. An example of such training example may include a surgical image or video of a sample surgical procedure associated with a sample time sensitive situation, together with a label indicating a selection of a desired time period for initiating an action to address the sample time sensitive situation. Step 930 may use the trained machine learning model to analyze the first surgical footage received by Step 910 to select the time period for initiating the action to address the time sensitive situation. In some examples, an urgency level associated with the time sensitive situation may be determined, and Step 930 may select the time period for initiating the action to address the time sensitive situation based on the determined urgency level. In one example, a visual classification model may be used to classify the time sensitive situation identified by Step 920 to one of a plurality of alternative classes, each alternative class may be associated with a different urgency level, and thereby the urgency level associated with the time sensitive situation may be determined. In some examples, the selection of the time period for initiating the action to address the time sensitive situation by Step 930 may be based on a patient associated with the ongoing surgical procedure. For example, when the patient has a particular characteristic (such as 'Age over 70', 'Obese', a particular medical condition, etc.), Step 930 may select a shorter time period, and when the patient does not have the particular characteristic, Step may select a longer time period.

In some examples, Step 940 may comprise receiving second surgical footage captured using the at least one image sensor from the ongoing surgical procedure after the identification of the time sensitive situation. For example, the received second surgical footage may include surgical footage captured using at least one of overhead camera 115, overhead camera 121, overhead camera 123, tableside camera 125 or image sensors 421. In some examples, receiving the second surgical footage by Step 940 may include reading the second surgical footage from memory. In some examples, receiving the second surgical footage by Step 940 may include receiving the second surgical footage from an external device, for example using a digital communication device via a digital communication line or a digital communication network. In some examples, receiving the second surgical footage by Step 940 may include capturing the second surgical footage using the at least one image sensor.

In some examples, Step 950 may comprise analyzing surgical footage (such as the second surgical footage received by Step 940) to determine that no action to address a time sensitive situation (such as the time sensitive situation identified by Step 920) was initiated within a selected time period (such as the time period selected by Step 930). For example, Step 950 may use a visual action recognition algorithm to analyze the second surgical footage received by Step 940 to determine a plurality of actions in the ongoing surgical procedure after the identification of the time sensitive situation by Step 920. The determined plurality of actions may be analyzed to determine whether an action to address the time sensitive situation identified by Step 920 was initiated within the time period selected by Step 930. In another example, a machine learning model may be trained using training examples to determine whether actions to address time sensitive situations were initiated in different time periods from images and/or videos. An example of such training example may include a surgical image or video of a sample surgical procedure associated with a sample time sensitive situation, together with a label indicating whether an action to address the sample time sensitive situation was initiated in a particular time period. Step 950 may use the trained machine learning model to analyze the second surgical footage received by Step 940 to determine whether an action to address the time sensitive situation identified by Step 920 was initiated within the time period selected by Step 930. In yet another example, Step 950 may analyze at least part of the second surgical footage received by Step 940 to calculate a convolution of the at least part of the second surgical footage and thereby obtain a result value of the calculated convolution. In one example, in response to the result value of the calculated convolution being a first value, Step 950 may determine that no action to address the time sensitive situation identified by Step 920 was initiated within the time period selected by Step 930, and in response to the result value of the calculated convolution being a second value, Step 950 may determine that an action to address the time sensitive situation identified by Step 920 was initiated within the time period selected by Step 930.

In some examples, surgical footage (such as the second surgical footage received by Step 940) may be analyzed to detect a surgical instrument, for example using a visual object detection algorithm. In some examples, surgical footage (such as the second surgical footage received by Step 940) may be analyzed to determine a type of the surgical instrument, for example using a visual object recognition algorithm. In some examples, a relationship between the type of the surgical instrument and a time sensitive situation (such as the time sensitive situation identified by Step 920) may be determined. For example, a data structure associating types of the surgical instruments with types of time sensitive situations may be accessed based on the determined type of the surgical instrument and the time sensitive situation identified by Step 920 to determine the relationship. In some examples, Step 950 may base the determination that no action to address the time sensitive situation was initiated within the selected time period on the relationship between the type of the surgical instrument and the time sensitive situation. For example, when there is a relation between the type of the surgical instrument and the time sensitive situation, Step 950 may determine that an action to address the time sensitive situation was initiated within the selected time period, and when there is no relation between the type of the surgical instrument and the time sensitive situation, Step 950 may determine that no action to address the time sensitive situation was initiated within the selected time period.

In some examples, surgical footage (such as the second surgical footage received by Step 940) may be analyzed to detect an interaction between a surgical instrument and an anatomical structure. For example, the surgical footage may be analyzed using a visual object detection algorithm to detect the surgical instrument and the anatomical structure and their positions, and the positions of the two may be compared. When the two are adjacent, an interaction between the surgical instrument and the anatomical structure may be detected, and when the two are remote from one another, no interaction between the surgical instrument and the anatomical structure may be detected. In another example, the surgical footage may be analyzed using a visual motion detection algorithm to detect relative motion between the surgical instrument and the anatomical structure. When the two are approaching each other, an interaction between the surgical instrument and the anatomical structure may be detected, and when the two are moving away from one another, no interaction between the surgical instrument and the anatomical structure may be detected. In yet another example, a machine learning model may be trained using training examples to detect interactions between surgical instruments and anatomical structures from images and/or videos. An example of such training example may include a surgical image or video of a sample surgical instrument and a sample anatomical structure, together with a label indicating whether there is an interaction between the sample surgical instrument and the sample anatomical structure. The trained machine learning model may be used to analyze the second surgical footage received by Step 940 to detect the interaction between the surgical instrument and the anatomical structure. In some examples, Step 950 may base the determination that no action to address the time sensitive situation was initiated within the selected time period on the interaction. For example, when no interaction between the surgical instrument and the anatomical structure is detected, Step 950 may determine that no action to address the time sensitive situation was initiated within the selected time period, and when an interaction between the surgical instrument and the anatomical structure is detected, Step 950 may determine that an action to address the time sensitive situation was initiated within the selected time period. In another example, a type of the detected interaction between the surgical instrument and the anatomical structure may be determined, for example by classifying the interaction using a classification algorithm, and Step 950 may base the determination that no action to address the time sensitive situation was initiated within the selected time period on the type of the interaction. For example, when the detected interaction between the surgical instrument and the anatomical structure is an interaction of a first type, Step 950 may determine that no action to address the time sensitive situation was initiated within the selected time period, and when the detected interaction between the surgical instrument and the anatomical structure is an interaction of a second type, Step 950 may determine that an action to address the time sensitive situation was initiated within the selected time period.

In some examples, surgical footage (such as the second surgical footage received by Step 940) may be analyzed to detect one or more surgical actions, for example using a visual action recognition algorithm. In one example, the detection of a surgical action may include a determination of a type of the surgical action. In some examples, Step 950 may base the determination that no action to address the time sensitive situation was initiated within the selected time period on the detected one or more surgical actions. For example, when a surgical action of a particular type is not detected, Step 950 may determine that no action to address the time sensitive situation was initiated within the selected time period, and when a surgical action of the particular type is detected, Step 950 may determine that an action to address the time sensitive situation was initiated within the selected time period.

In some examples, Step 960 may comprise, in response to the determination by Step 950 that no action to address the time sensitive situation was initiated within the selected time period, providing information indicative of a need to address the time sensitive situation. For example, Step 960 may provide the information indicative of the need to address the time sensitive situation to a memory unit to cause the memory unit to store selected data. In another example. Step 960 may provide the information indicative of the need to address the time sensitive situation to an external device, for example by transmitting, using a digital communication device over a digital communication line or digital communication network, a digital signal encoding the information. In yet another example, Step 960 may provide the information indicative of the need to address the time sensitive situation to a person, for example audibly, visually, graphically, textually, via a user interface, and so forth. For example, Step 960 may provide the information indicative of the need to address the time sensitive situation to a surgeon performing the ongoing surgical procedure. In another example, Step 960 may provide the information indicative of the need to address the time sensitive situation to a person outside an operating room (the person may be associated with the ongoing surgical procedure, for example, a supervisor of the surgeon performing the ongoing surgical procedure).

In some examples, surgical footage (such as the second surgical footage received by Step 940) may be analyzed to detect a surgical action unrelated to the time sensitive situation. In some examples, the surgical footage may be analyzed using a visual action recognition algorithm to detect a plurality of surgical actions. In one example, each surgical action of the plurality of surgical actions may be classified as a surgical action related to the time sensitive situation or surgical action unrelated to the time sensitive situation, for example using a visual classification algorithm. In another example, a type of each surgical action of the plurality of surgical actions may be determined, for example by classifying the surgical action to one of a plurality of classes, where each class corresponds to a type. Further, a data structure associating types of surgical actions with types of time sensitive situation may be accessed to determine whether any one of the plurality of surgical actions is unrelated to the time sensitive situation, thereby detecting the surgical action unrelated to the time sensitive situation. In some examples, an urgency corresponding to the surgical action unrelated to the time sensitive situation may be determined. In one example, a visual classification model may be used to classify the detected surgical action unrelated to the time sensitive situation to one of a plurality of alternative classes, each alternative class may be associated with a different urgency level, and thereby the urgency level associated with the detected surgical action unrelated to the time sensitive situation may be determined. In some examples, Step 960 may provide the information indicative of the need to address the time sensitive situation when the determined urgency is below a selected threshold, and may withhold providing the information indicative of the need to address the time sensitive situation when the determined urgency is above the selected threshold. In some examples, the threshold may be selected based on a type of the ongoing surgical procedure. For example, when the ongoing surgical procedure is an elective surgery, a lower threshold may be selected, and when the ongoing surgical procedure is an emergency surgery, a higher threshold may be selected. In another example, when the ongoing surgical procedure is an open surgery, a lower threshold may be selected, and when the ongoing surgical procedure is a minimal invasive surgery, a higher threshold may be selected. In yet another example, when the ongoing surgical procedure is a transplantation surgery, one threshold may be selected, and when the ongoing surgical procedure is a urologic surgery, another threshold may be selected. In some examples, the threshold may be selected based on a patient associated with the ongoing surgical procedure. For example, when the patient has a particular characteristic (such as 'Age over 70', 'Obese', a particular medical condition, etc.), a higher threshold may be selected, and when the patient does not have the particular characteristic, a lower threshold may be selected. In some examples, the threshold may be selected based on a state of an anatomical structure. For example, surgical footage (such as the second surgical footage received by Step 940) may be analyzed to determine a state of an anatomical structure, and the threshold may be selected based on the determined state of the anatomical structure. For example, when the state of the anatomical structure is one state (such as 'In poor condition', 'Without blood flow', 'Injured', etc.), a higher threshold may be selected, and when the state of the anatomical structure is another state (such as 'In good condition', 'With sufficient blood flow', 'Intact', etc.), a lower threshold may be selected. In one example, the surgical footage may be classified using a visual classification algorithm to one of a plurality of alternative classes, each alternative class may correspond to a state of the anatomical structure, and thereby the state of the anatomical structure may be determined.

In some examples, surgical footage (such as the second surgical footage received by Step 940) may be analyzed to identify a second time sensitive situation. For example, the analysis of the second surgical footage received by Step 940 for identifying the second time sensitive situation may be similar to the analysis of the first surgical footage for identifying the time sensitive situation by Step 920. In one example, in response to the identification of the second time sensitive situation, the selection of the time period by Step 930 may be updated. For example, the time period may be extended or delayed in response to the identification of the second time sensitive situation.

In some examples, surgical footage (such as the second surgical footage received by Step 940) may be analyzed to determine that an action to address a second time sensitive situation is undergoing. For example, a machine learning model may be trained using training examples to identify time sensitive situations and undergoing actions for addressing the time sensitive situations from images and/or videos. An example of such training example may include a surgical image or video of a sample surgical procedure, together with a label indicating a time sensitive situation associated with the sample surgical procedure, and an undergoing action in the sample surgical procedure for addressing the time sensitive situation associated with the sample surgical procedure. The trained machine learning model may be used to analyze the second surgical footage received by Step 940 to identify a particular time sensitive situation different than the time sensitive situation identified by Step 920 (i.e., the second time sensitive situation) and an undergoing action to address the particular time sensitive situation. In some examples, Step 960 may withhold providing the information indicative of the need to address the time sensitive situation until the action to address the second time sensitive situation is completed. For example, the second surgical footage received by Step 940 may be analyzed using an action recognition algorithm to determine when the action to address the second time sensitive situation is completed, and after the action is completed, Step 960 may provide the information indicative of the need to address the time sensitive situation.

In some examples, third surgical footage captured using the at least one image sensor from the ongoing surgical procedure after the information indicative of the need to address the time sensitive situation is provided by Step 960 may be received. For example, the received third surgical footage may include surgical footage captured using at least one of overhead camera 115, overhead camera 121, overhead camera 123, tableside camera 125 or image sensors 421. In some examples, receiving the third surgical footage by Step 940 may include reading the third surgical footage from memory. In some examples, receiving the third surgical footage by Step 940 may include receiving the third surgical footage from an external device, for example using a digital communication device via a digital communication line or a digital communication network. In some examples, receiving the third surgical footage by Step 940 may include capturing the third surgical footage using the at least one image sensor. In some examples, the third surgical footage may be analyzed to determine that no action to address the time sensitive situation was initiated within a second time period, for example as described above in relation to the second surgical footage and Step 950. In some examples, in response to the determination that no action to address the time sensitive situation was initiated within the second time period, second information indicative of the need to address the time sensitive situation may be provided. In one example, the second information may differ from the first information. In one example, the second information may be of greater intensity than the first information. For example, the second information indicative of the need to address the time sensitive situation may be provided to a memory unit to cause the memory unit to store selected data. In another example, the second information indicative of the need to address the time sensitive situation may be provided to an external device, for example by transmitting, using a digital communication device over a digital communication line or digital communication network, a digital signal encoding the second information. In yet another example, the second information indicative of the need to address the time sensitive situation may be provided to a person, for example audibly, visually, graphically, textually, via a user interface, and so forth.

In some examples, third surgical footage captured using the at least one image sensor from the ongoing surgical procedure after the information indicative of the need to address the time sensitive situation is provided by Step 960 may be received, for example as described above. In some examples, the third surgical footage may be analyzed to determine that an action to address the time sensitive situation identified by Step 920 was initiated within a second time period, for example as described above in relation to the second surgical footage and Step 950. In some example, it may be determined that the initiated action is insufficient to successfully address the time sensitive situation identified by Step 920. For example, a machine learning model may be trained using training examples to determine whether actions are sufficient to successfully address time sensitive situations from images and/or videos. An example of such training example may include a surgical image or video or a sample action, together with a label indicating whether the sample action is sufficient to successfully address a particular time sensitive situation. The trained machine learning model may be used to analyze the third surgical footage and determine that the initiated action is insufficient to successfully address the time sensitive situation identified by Step 920. In some examples, in response to the determination that the initiated action is insufficient to successfully address the time sensitive situation, second information may be provided. For example, the second information may include an indication that the initiated action is insufficient to successfully address the time sensitive situation. In one example, the second information may be provided to a memory unit to cause the memory unit to store selected data. In another example, the second information may be provided to an external device, for example by transmitting, using a digital communication device over a digital communication line or digital communication network, a digital signal encoding the second information. In yet another example, the second information may be provided to a person, for example audibly, visually, graphically, textually, via a user interface, and so forth.

Figure 10:
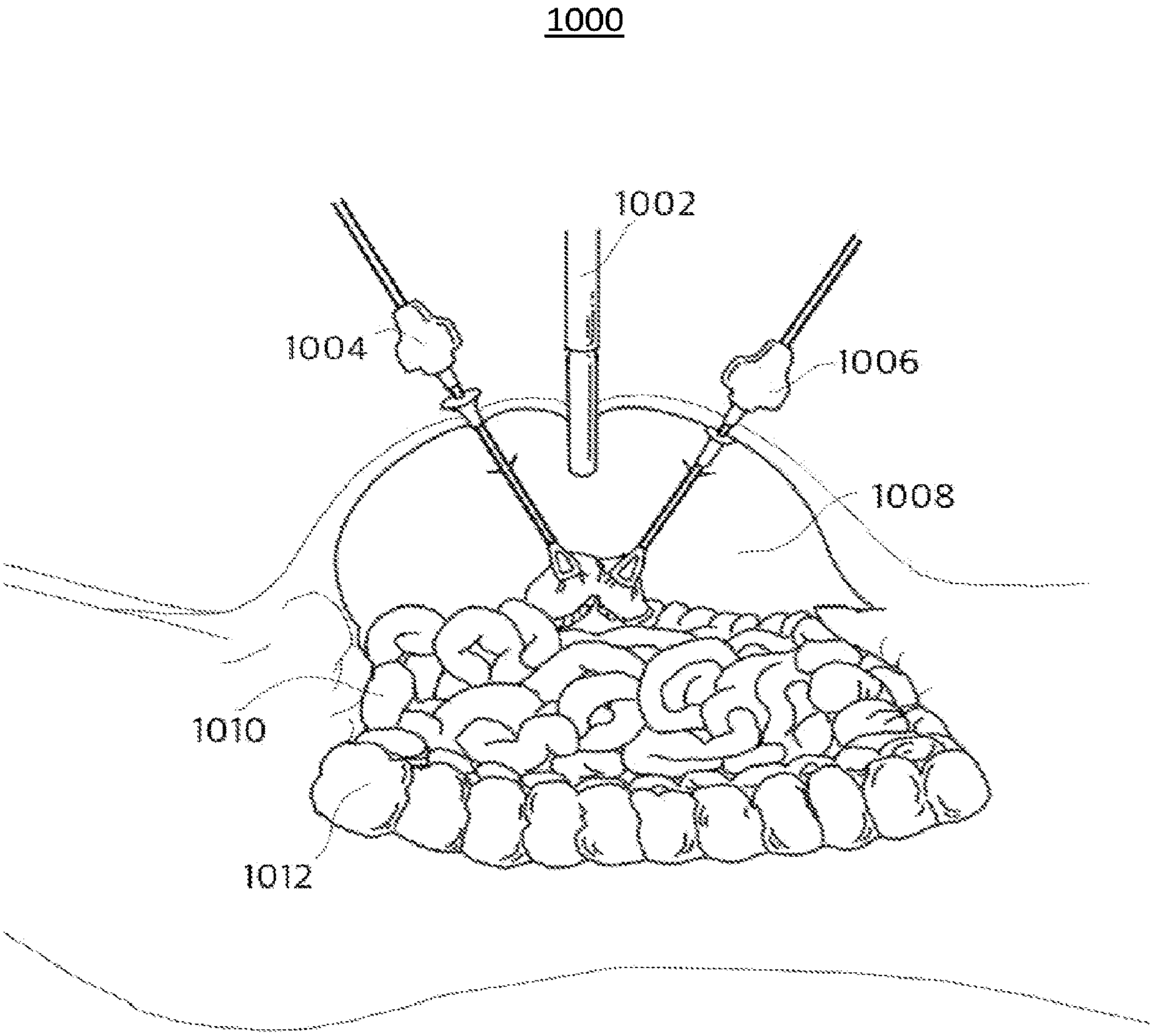
FIG. 10 is a perspective view of an exemplary laparoscopic surgery, consistent with disclosed embodiments.

FIG. 10 is a perspective view of an exemplary laparoscopic surgery 1000, consistent with disclosed embodiments. In this example, small intestine 1010 and large intestine 1012 are in abdomen 1008. Abdomen 1008 that is filled with gas, which creates a surgical cavity in abdomen 1008. Laparoscope 1002 captures surgical footage from the surgical cavity in abdomen 1008. Two surgical tools 1004 and 1006 are in abdomen 1008 and interact with small intestine 1010.

In the example of FIG. 10, Step 710 may receive surgical footage of the ongoing surgical procedure 1000 captured using laparoscope 1002. Step 720 may analyze the surgical footage of the ongoing surgical procedure 1000 to detect a presence of surgical instrument 1004 in the surgical cavity in abdomen 1008 at a particular time. Step 730 may analyze the surgical footage of the ongoing surgical procedure 1000 to determine a phase of the ongoing surgical procedure 1000 at the particular time. Step 740 may, based on the presence of surgical instrument 1004 in the surgical cavity in abdomen 1008 at the particular time and the determined phase of the ongoing surgical procedure 1000 at the particular time, determine a likelihood that a prospective action involving surgical instrument 1004 is about to take place at an unsuitable phase of the ongoing surgical procedure 1000. Step 750 may, based on the determined likelihood, provide a digital signal before the prospective action takes place.

In the example of FIG. 10, Step 810 may receive surgical footage of ongoing surgical procedure 1000 performed on a patient captured using laparoscope 1002, the ongoing surgical procedure 1000 is associated with a known condition of the patient. Step 820 may analyze the surgical footage captured using laparoscope 1002 to determine a likelihood that a feasible biopsy will cause a diagnosis of a condition other than the known condition of the patient. Step 830 may, based on the determined likelihood, provide a digital signal configured to cause a removal of a sample of a tissue for the feasible biopsy during the ongoing surgical procedure. For example, the known condition of the patient may be associated with small intestine 1010 and not associated with large intestine 1012 (for example, abscess in small intestine 1010), and the condition other than the known condition of the patient may be associated with large intestine 1012 (for example, colon cancer).

In the example of FIG. 10, Step 910 may receive first surgical footage captured using laparoscope 1002 from ongoing surgical procedure 1000. Step 920 may analyze the first surgical footage to identify a time sensitive situation. Step 930 may select a time period for initiating an action to address the time sensitive situation. Step 940 may receive second surgical footage captured using laparoscope 1002 from the ongoing surgical procedure after the identification of the time sensitive situation. Step 950 may analyze the second surgical footage to determine that no action to address the time sensitive situation was initiated within the selected time period. Step 960 may, for example in response to the determination that no action to address the time sensitive situation was initiated within the selected time period, provide information indicative of a need to address the time sensitive situation. For example, the time sensitive situation identified by Step 920 may be associated with large intestine 1012, and Step 950 may determine that no action to address the time sensitive situation was initiated within the selected time period based on a determination that no surgical tool interacts with large intestine 1012, for example as surgical tools 1004 and 1006 interact with small intestine 1010.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium including instructions that, when executed by at least one processor, cause the at least one processor to perform operations for addressing time sensitive situations in surgical procedures, the operations comprising:

receiving first surgical footage captured using at least one image sensor from an ongoing surgical procedure;

analyzing the first surgical footage to identify a time sensitive situation;

selecting a time period for initiating an action to address the time sensitive situation;

receiving second surgical footage captured using the at least one image sensor from the ongoing surgical procedure after the identification of the time sensitive situation;

analyzing the second surgical footage to determine that no action to address the time sensitive situation was initiated within the selected time period;

in response to the determination that no action to address the time sensitive situation was initiated within the selected time period, providing information indicative of a need to address the time sensitive situation;

analyzing the second surgical footage to determine that an action to address a second time sensitive situation is undergoing; and withholding providing the information indicative of the need to address the time sensitive situation until the action to address the second time sensitive situation is completed.

2. The non-transitory computer readable medium of claim 1, wherein the time sensitive situation includes at least one of a bleeding, leakage, blockage of blood flow, or compression.

3. The non-transitory computer readable medium of claim 1, wherein the operations further comprises analyzing the first surgical footage to select the time period for initiating the action to address the time sensitive situation.

4. The non-transitory computer readable medium of claim 1, wherein the selection of the time period for initiating the action to address the time sensitive situation is based on a patient associated with the ongoing surgical procedure.

5. The non-transitory computer readable medium of claim 1, wherein the operations further comprises providing second information in response to the identification of the time sensitive situation, the second information differs from the information provided in response to the determination that no action to address the time sensitive situation was initiated within the selected time period.

6. The non-transitory computer readable medium of claim 1, wherein the operations further comprising:

analyzing the second surgical footage to detect a surgical instrument;

analyzing the second surgical footage to determine a type of the surgical instrument;

determining a relationship between the type of the surgical instrument and the time sensitive situation; and basing the determination that no action to address the time sensitive situation was initiated within the selected time period on the relationship between the type of the surgical instrument and the time sensitive situation.

7. The non-transitory computer readable medium of claim 1, wherein the operations further comprising:

analyzing the second surgical footage to detect an interaction between a surgical instrument and an anatomical structure; and basing the determination that no action to address the time sensitive situation was initiated within the selected time period on the interaction.

8. The non-transitory computer readable medium of claim 1, wherein the operations further comprising:

analyzing the second surgical footage to detect one or more surgical actions; and basing the determination that no action to address the time sensitive situation was initiated within the selected time period on the detected one or more surgical actions.

9. The non-transitory computer readable medium of claim 1, wherein the operations further comprising:

analyzing the second surgical footage to detect a surgical action unrelated to the time sensitive situation;

determining an urgency corresponding to the surgical action unrelated to the time sensitive situation; and providing the information indicative of the need to address the time sensitive situation when the determined urgency is below a selected threshold.

10. The non-transitory computer readable medium of claim 9, wherein the threshold is selected based on a type of the ongoing surgical procedure.

11. The non-transitory computer readable medium of claim 9, wherein the threshold is selected based on a patient associated with the ongoing surgical procedure.

12. The non-transitory computer readable medium of claim 9, wherein the operations further comprising:

analyzing the second surgical footage to determine a state of an anatomical structure; and selecting the threshold based on the state of the anatomical structure.

13. The non-transitory computer readable medium of claim 1, wherein the operations further comprising:

in response to the identification of the second time sensitive situation, updating the selection of the time period.

14. The non-transitory computer readable medium of claim 1, wherein the operations further comprising:

receiving third surgical footage captured using the at least one image sensor from the ongoing surgical procedure after the information indicative of the need to address the time sensitive situation is provided;

analyzing the third surgical footage to determine that no action to address the time sensitive situation was initiated within a second time period; and in response to the determination that no action to address the time sensitive situation was initiated within the second time period, providing second information indicative of the need to address the time sensitive situation, the second information is of greater intensity than the first information.

15. The non-transitory computer readable medium of claim 1, wherein the operations further comprising:

receiving third surgical footage captured using the at least one image sensor from the ongoing surgical procedure after the information indicative of the need to address the time sensitive situation is provided;

analyzing the third surgical footage to determine that an action to address the time sensitive situation was initiated within a second time period;

determining that the initiated action is insufficient to successfully address the time sensitive situation; and in response to the determination that the initiated action is insufficient to successfully address the time sensitive situation, providing second information.

16. The non-transitory computer readable medium of claim 1, wherein the information is provided to a surgeon performing the ongoing surgical procedure.

17. The non-transitory computer readable medium of claim 1, wherein the information is provided to a person outside an operating room, the person is associated with the ongoing surgical procedure.

18. A system for addressing time sensitive situations in surgical procedures, the system comprising:

at least one processor configured to:

receive first surgical footage captured using at least one image sensor from an ongoing surgical procedure;

analyze the first surgical footage to identify a time sensitive situation;

select a time period for initiating an action to address the time sensitive situation;

receive second surgical footage captured using the at least one image sensor from the ongoing surgical procedure after the identification of the time sensitive situation;

analyze the second surgical footage to determine that no action to address the time sensitive situation was initiated within the selected time period;

in response to the determination that no action to address the time sensitive situation was initiated within the selected time period, provide information indicative of a need to address the time sensitive situation;

analyze the second surgical footage to determine that an action to address a second time sensitive situation is undergoing; and withhold providing the information indicative of the need to address the time sensitive situation until the action to address the second time sensitive situation is completed.

19. A method for addressing time sensitive situations in surgical procedures, the method comprising:

receiving first surgical footage captured using at least one image sensor from an ongoing surgical procedure;

analyzing the first surgical footage to identify a time sensitive situation;

selecting a time period for initiating an action to address the time sensitive situation;

receiving second surgical footage captured using the at least one image sensor from the ongoing surgical procedure after the identification of the time sensitive situation;

analyzing the second surgical footage to determine that no action to address the time sensitive situation was initiated within the selected time period;

in response to the determination that no action to address the time sensitive situation was initiated within the selected time period, providing information indicative of a need to address the time sensitive situation;

analyzing the second surgical footage to determine that an action to address a second time sensitive situation is undergoing; and withholding providing the information indicative of the need to address the time sensitive situation until the action to address the second time sensitive situation is completed.

20. A non-transitory computer readable medium including instructions that, when executed by at least one processor, cause the at least one processor to perform operations for addressing time sensitive situations in surgical procedures, the operations comprising:

receiving first surgical footage captured using at least one image sensor from an ongoing surgical procedure;

analyzing the first surgical footage to identify a time sensitive situation;

selecting a time period for initiating an action to address the time sensitive situation;

receiving second surgical footage captured using the at least one image sensor from the ongoing surgical procedure after the identification of the time sensitive situation;

analyzing the second surgical footage to determine that no action to address the time sensitive situation was initiated within the selected time period;

in response to the determination that no action to address the time sensitive situation was initiated within the selected time period, providing information indicative of a need to address the time sensitive situation;

analyzing the second surgical footage to detect a surgical action unrelated to the time sensitive situation;

determining an urgency corresponding to the surgical action unrelated to the time sensitive situation; and providing the information indicative of the need to address the time sensitive situation when the determined urgency is below a selected threshold.

* * * * *